US009330675B2

(12) United States Patent
Zhang et al.

(10) Patent No.: US 9,330,675 B2
(45) Date of Patent: May 3, 2016

(54) METHOD AND APPARATUS FOR WIND NOISE DETECTION AND SUPPRESSION USING MULTIPLE MICROPHONES

(75) Inventors: Xianxian Zhang, San Diego, CA (US); Juin-Hwey Chen, Irvine, CA (US); Huaiyu Zeng, Red Bank, NJ (US); Jes Thyssen, San Juan Capistrano, CA (US)

(73) Assignee: Broadcom Corporation, Irvine, CA (US)

( * ) Notice: Subject to any disclaimer, the term of this patent is extended or adjusted under 35 U.S.C. 154(b) by 1058 days.

(21) Appl. No.: 13/250,355

(22) Filed: Sep. 30, 2011

(65) Prior Publication Data

US 2012/0121100 A1 May 17, 2012

Related U.S. Application Data

(60) Provisional application No. 61/413,231, filed on Nov. 12, 2010.

(51) Int. Cl.

| | |
|---|---|
| ***A61F 11/06*** | (2006.01) |
| ***G10L 21/0208*** | (2013.01) |
| ***G10L 21/0272*** | (2013.01) |
| ***H04R 1/24*** | (2006.01) |
| *G10L 21/0216* | (2013.01) |

(52) U.S. Cl.

CPC ......... *G10L 21/0208* (2013.01); *G10L 21/0272* (2013.01); *H04R 1/245* (2013.01); *G10L 2021/02165* (2013.01); *H04R 2410/07* (2013.01)

(58) Field of Classification Search

CPC .. H04R 2410/07; H04R 3/005; H04R 25/407; H04R 2430/23; H04R 2225/41; H04R 2430/03; H04R 25/505; H04R 2430/20; H04R 2499/13; H04R 1/406; H04R 2225/43; H04R 2410/05; H04R 2420/07; H04R 2430/25; H04R 2499/11

USPC ............... 381/92, 71.1–71.8, 94.1–94.4, 317; 704/223–227; 455/296

See application file for complete search history.

(56) References Cited

U.S. PATENT DOCUMENTS

| | | | |
|---|---|---|---|
| 4,570,746 | A | 2/1986 | Das et al. |
| 4,600,077 | A | 7/1986 | Drever |
| 5,288,955 | A | 2/1994 | Staple et al. |
| 5,550,924 | A | 8/1996 | Helf et al. |
| 5,574,824 | A | 11/1996 | Slyh et al. |
| 5,757,937 | A | 5/1998 | Itoh et al. |
| 5,943,429 | A | 8/1999 | Handel |
| 6,230,123 | B1 | 5/2001 | Mekuria et al. |
| 7,099,821 | B2 | 8/2006 | Visser et al. |
| 7,359,504 | B1 | 4/2008 | Reuss et al. |
| 7,464,029 | B2 | 12/2008 | Visser et al. |
| 7,617,099 | B2 | 11/2009 | Yank et al. |
| 7,916,882 | B2 | 3/2011 | Pedersen et al. |
| 7,949,520 | B2 | 5/2011 | Nongpiur et al. |

(Continued)

*Primary Examiner* — Lun-See Lao

(74) *Attorney, Agent, or Firm* — Sterne, Kessler, Goldstein & Fox P.L.L.C.

(57) ABSTRACT

Unlike sound based pressure waves that go everywhere, air turbulence caused by wind is usually a fairly local event. Therefore, in a system that utilizes two or more spatially separated microphones to pick up sound signals (e.g., speech), wind noise picked up by one of the microphones often will not be picked up (or at least not to the same extent) by the other microphone(s). Embodiments of methods and apparatuses that utilize this tact and others to effectively detect and suppress wind noise using multiple microphones that are spatially separated are described.

20 Claims, 14 Drawing Sheets

(56) References Cited

U.S. PATENT DOCUMENTS

| | | | | |
|---|---|---|---|---|
| 7,983,907 | B2 | 7/2011 | Visser et al. | |
| 8,150,682 | B2 | 4/2012 | Nongpiur et al. | |
| 8,340,309 | B2 | 12/2012 | Burnett et al. | |
| 8,374,358 | B2 | 2/2013 | Buck et al. | |
| 8,452,023 | B2 * | 5/2013 | Petit et al. | 381/71.8 |
| 8,515,097 | B2 | 8/2013 | Nemer et al. | |
| 2005/0036629 | A1 | 2/2005 | Aubauer et al. | |
| 2006/0193671 | A1 | 8/2006 | Yoshizawa et al. | |
| 2007/0021958 | A1 | 1/2007 | Visser et al. | |
| 2007/0030989 | A1 * | 2/2007 | Kates | 381/317 |
| 2007/0033029 | A1 | 2/2007 | Sakawaki | |
| 2008/0025527 | A1 | 1/2008 | Haulick et al. | |
| 2008/0033584 | A1 | 2/2008 | Zopf et al. | |
| 2008/0046248 | A1 | 2/2008 | Chen et al. | |
| 2008/0201138 | A1 | 8/2008 | Visser et al. | |
| 2010/0008519 | A1 | 1/2010 | Hayakawa et al. | |
| 2010/0223054 | A1 * | 9/2010 | Nemer et al. | 704/219 |
| 2010/0254541 | A1 * | 10/2010 | Hayakawa | 381/71.1 |
| 2010/0260346 | A1 | 10/2010 | Takano et al. | |
| 2011/0038489 | A1 | 2/2011 | Visser et al. | |
| 2011/0099007 | A1 | 4/2011 | Zhang | |
| 2011/0099010 | A1 | 4/2011 | Zhang | |
| 2011/0103626 | A1 | 5/2011 | Bisgaard et al. | |
| 2012/0010882 | A1 | 1/2012 | Thyssen et al. | |
| 2012/0123771 | A1 | 5/2012 | Chen et al. | |
| 2012/0123772 | A1 | 5/2012 | Thyssen et al. | |
| 2012/0123773 | A1 | 5/2012 | Zeng et al. | |
| 2013/0044872 | A1 | 2/2013 | Eriksson et al. | |
| 2013/0211830 | A1 | 8/2013 | Petit et al. | |

* cited by examiner

800

METHOD AND APPARATUS FOR WIND NOISE DETECTION AND SUPPRESSION USING MULTIPLE MICROPHONES

CROSS REFERENCE TO RELATED APPLICATIONS

This application claims the benefit of U.S. Provisional Patent Application No. 61/413,231, filed on Nov. 12, 2010, which is incorporated herein by reference in its entirety.

FIELD OF THE INVENTION

This application relates generally to noise detection and suppression and, more particularly to, wind noise detection and suppression.

BACKGROUND

A speech signal picked up by a microphone can be corrupted by acoustic noise present in the environment surrounding the microphone as well as by certain system-introduced noise, such as noise introduced by quantization and channel interference. If no attempt is made to mitigate the impact of the noise, the corruption of the speech signal will result in a degradation of its perceived quality and intelligibility when played back to a listener. The corruption of the speech signal can also adversely impact the performance of speech coding and recognition algorithms.

One additional source of noise that can corrupt the speech signal picked up by the microphone is wind. Wind causes turbulence in air flow and, if this turbulence impacts the microphone, it can result in the microphone picking up sound referred to as "wind noise." In general, wind noise is bursty in nature and can last from a few milliseconds up to a few hundred milliseconds or more. Because wind noise is impulsive and can exceed the nominal amplitude of the speech signal, the presence of such noise will degrade the perceived quality and intelligibility of the speech signal. Furthermore, because wind noise is non-stationary in nature, it is typically not attenuated by noise suppression schemes conventionally used to suppress acoustic noise or system-introduced noise.

Therefore, what is needed is a method and apparatus that can effectively detect and suppress wind noise.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION

In the following description, numerous specific details are set forth in order to provide a thorough understanding of the invention. However, it will be apparent to those skilled in the art that the invention, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the invention.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

I. Overview

Unlike sound based pressure waves that go everywhere, air turbulence caused by wind is usually a fairly local event.

Therefore, in a system that utilizes two or more spatially separated microphones to pick up sound signals (e.g., speech), wind noise picked up by one of the microphones often will not be picked up (or at least not to the same extent) by the other microphone(s).

Described below are methods and apparatuses that utilize this fact and others to effectively detect and suppress wind noise using multiple microphones that are spatially separated. Before describing particular aspects of these methods and apparatuses, the discussion below begins by providing an example communication device and multi-microphone noise suppression system in which embodiments of the present invention can be implemented.

II. Example Operating Environment

Figure 1:
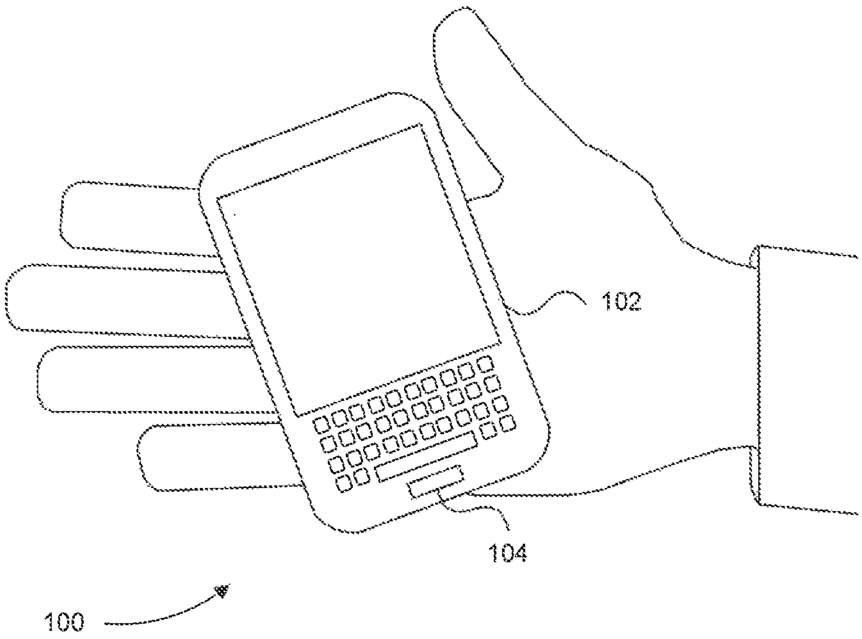
FIG. 1 illustrates a front view of an example wireless communication device in which embodiments of the preset invention can be implemented.
Figure 2:
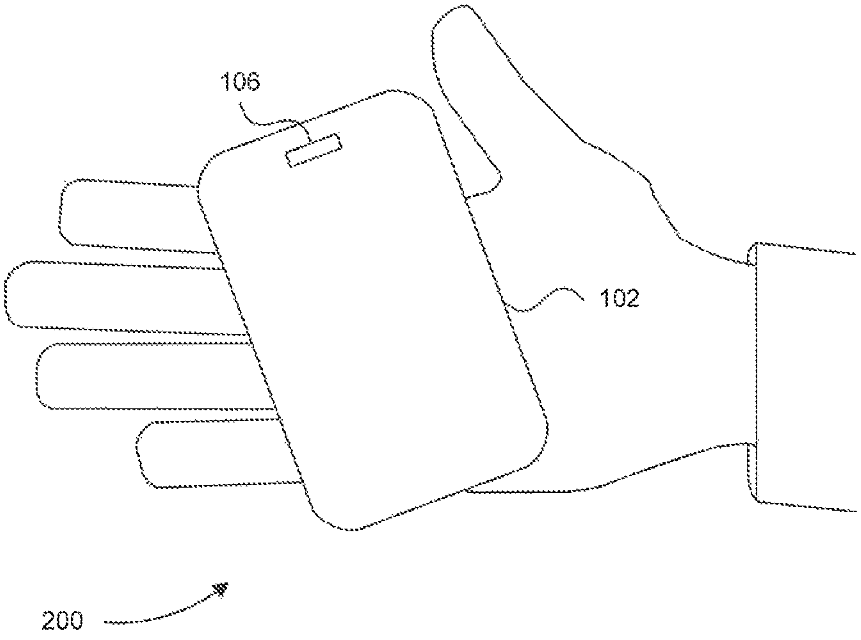
FIG. 2 illustrates a back view of the example wireless communication device shown in FIG. 1.

FIGS. 1 and 2 respectively illustrate a front portion 100 and a back portion 200 of an example wireless communication device 102 in which embodiments of the present invention can be implemented. Wireless communication device 102 can be a personal digital assistant (PDA), a cellular telephone, or a tablet computer, for example.

As shown in FIG. 1, front portion 100 of wireless communication device 102 includes a primary microphone 104 that is positioned to be proximate a user's mouth during regular use of wireless communication device 102. Accordingly, primary microphone 104 is positioned to detect the user's speech. As shown in FIG. 2, a back portion 200 of wireless communication device 102 includes a reference microphone 106 that is positioned to be farther from the user's mouth during regular use than primary microphone 104. For instance, reference microphone 106 can be positioned as far from the user's mouth during regular use as possible.

By positioning primary microphone 104 so that it is closer to the user's mouth than reference microphone 106 during regular use, a magnitude of the user's speech that is detected by primary microphone 104 is likely to be greater than a magnitude of the user's speech that is detected by reference microphone 106. This can be exploited to effectively suppress acoustic background noise as will be described further below in regard to FIG. 3.

In addition, because the two microphones 104 and 106 are spatially separated, wind noise picked up by one of the two microphones often will not be picked up (or at least not to the same extent) by the other microphone. This fact can be exploited to detect and suppress wind noise.

It should be noted that primary microphone 104 and reference microphone 106 are shown to be positioned on the respective front and back portions of wireless communication device 102 for illustrative purposes only and is not intended to be limiting. Persons skilled in the relevant art(s) will recognize that primary microphone 104 and reference microphone 106 can be positioned in any suitable locations on wireless communication device 102.

It should be further noted that a single reference microphone 106 is shown in FIG. 2 for illustrative purposes only and is not intended to be limiting. Persons skilled in the relevant art(s) will recognize that wireless communication device 102 can include any reasonable number of reference microphones.

Moreover, primary microphone 104 and reference microphone 106 are respectively shown in FIGS. 1 and 2 to be included in wireless communication device 102 for illustrative purposes only. It will be recognized by persons skilled in the relevant art(s) that primary microphone 104 and reference microphone 106 can be included in any suitable device (e.g., a non-wireless communication device, a Bluetooth® headset, a hearing aid, a personal recorder, a video recorder, and a sound pick-up system for public speech or on-stage performances).

Figure 3:
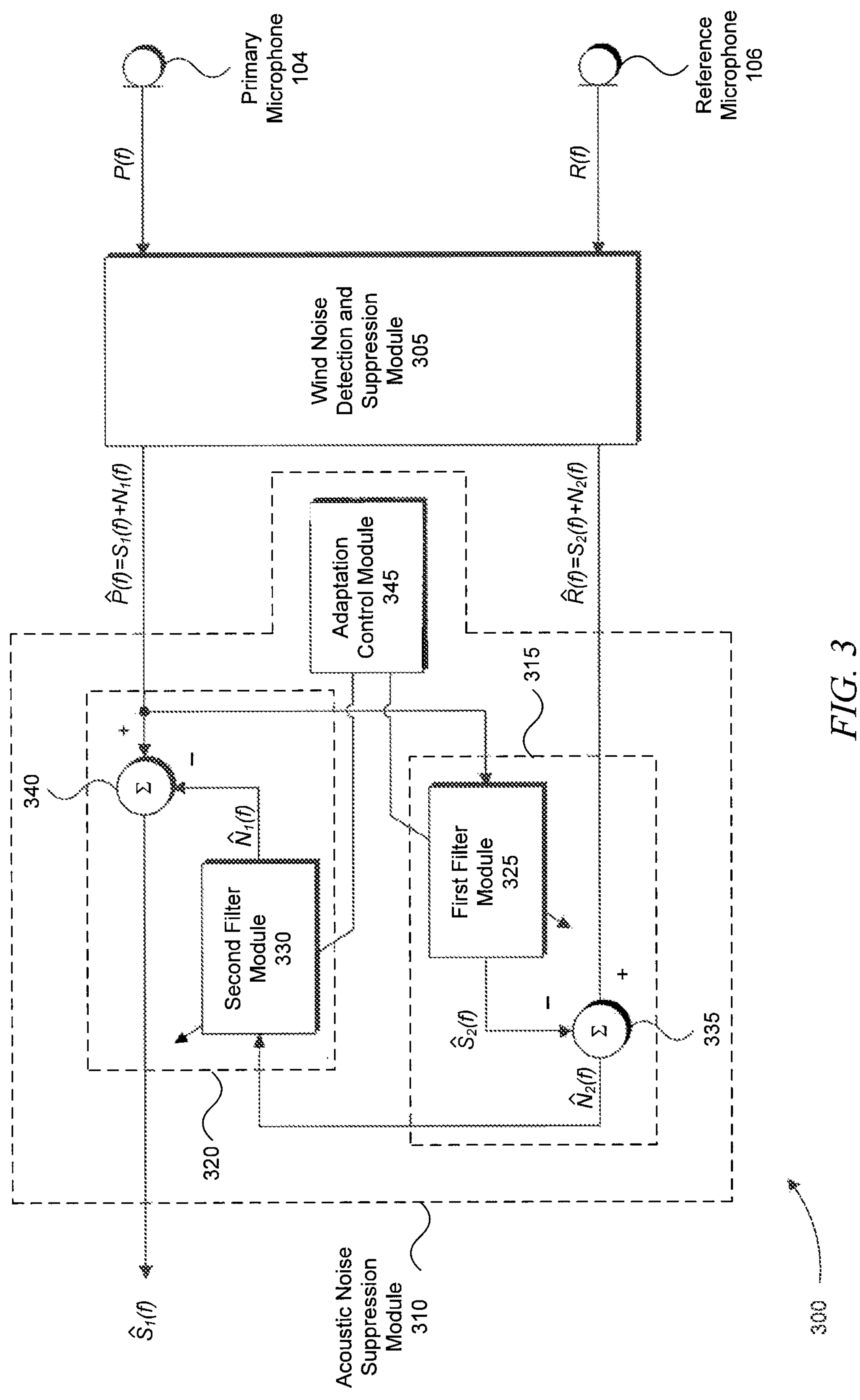
FIG. 3 illustrates a block diagram of an example multi-microphone noise suppression system that can be implemented in the example wireless communication device shown in FIG. 1.

Referring now to FIG. 3, a block diagram of an example multi-microphone noise suppression system 300 is illustrated. Multi-microphone noise suppression system 300 can be implemented in wireless communication device 102 to suppress wind and acoustic background noise that is associated with a primary signal P(f) (received by primary microphone 104) using a reference signal R(f) (received by reference microphone 106). As illustrated in FIG. 3, multi-microphone noise suppression system 300 specifically includes a wind noise detection and suppression module 305 for detecting and suppressing wind noise, followed by an acoustic noise suppression module 310 for suppressing acoustic background noise.

Ignoring the operational details of wind noise detection and suppression module 305 for the moment, acoustic noise suppression module 310 is configured to process a wind noise suppressed primary signal $\hat{P}(f)$ and a wind noise suppressed reference signal $\hat{R}(f)$ to remove acoustic background noise from $\hat{P}(f)$. In general, $\hat{P}(f)$ and $\hat{R}(f)$ respectively represent the residual signals of P(f) and R(f) after having undergone wind noise detection and, potentially, wind noise suppression by wind noise detection and suppression module 305. Both $\hat{P}(f)$ and $\hat{R}(f)$ contain components of the user's speech and acoustic background noise. However, because of the positioning of primary microphone 104 and reference microphone 106 on wireless communication device 102, the magnitude of the user's speech $S_1(f)$ in $\hat{P}(f)$ is likely to be greater than a magnitude of the user's speech $S_2(f)$ in $\hat{R}(f)$.

Acoustic noise suppression module 310 is configured to exploit this difference in magnitude to filter the wind noise suppressed primary signal $\hat{P}(f)$ using wind noise suppressed reference signal $\hat{R}(f)$ to provide, as output, speech signal $\hat{S}_1(f)$, which represents the acoustic and wind noise suppressed speech signal. As illustrated, acoustic noise suppression module 310 specifically includes a time-varying blocking matrix (BM) 315 and a time-varying active noise canceller (ANC) 320.

Time-varying BM 315 is configured to estimate and remove the undesirable speech component $S_2(f)$ in $\hat{R}(f)$ to get a "cleaner" noise reference signal. More specifically, time-varying BM 315 includes a first filter module 325 configured to filter $\hat{P}(f)$ to provide an estimate of the speech signal $S_2(f)$ in $\hat{R}(f)$. The estimated speech signal $\hat{S}_2(f)$ is then subtracted from $\hat{R}(f)$ by adder 335 to provide the cleaner noise reference signal $\hat{N}_2(f)$.

After the cleaner noise reference signal $\hat{N}_2(f)$ has been obtained, time-varying ANC 320 is configured to estimate and remove the undesirable acoustic background noise component $N_1(f)$ in $\hat{P}(f)$ to provide $\hat{S}_1(f)$. More specifically, time-varying ANC 320 includes a second filter module 330 configured to filter the cleaner noise reference signal $\hat{N}_2(f)$ to provide an estimate of the acoustic background noise $N_1(f)$ in $\hat{P}(f)$. The estimated background noise $\hat{N}_1(f)$ is then subtracted from $\hat{P}(f)$ by adder 340 to provide the acoustic and wind noise suppressed speech signal $\hat{S}_1(f)$.

Acoustic noise suppression module 310 further includes an adaptation control module 345 configured to update tap coefficients of first filter module 325 and second filter module 330 to provide the desired filter functionality described above. In an embodiment, first filter module 325 and second filter module 330 are configured to respectively filter $\hat{P}(f)$ and $\hat{N}_2(f)$ in the frequency domain using one or more taps per frequency component in signals $\hat{P}(f)$ and $\hat{N}_2(f)$. In another embodiment, first filter module 325 and second filter module 330 are configured to respectively filter these two signals in the time domain.

In at least one embodiment, and as further shown in FIG. 3, wind noise detection and suppression module 305 is configured to process primary signal P(f) and reference signal R(f) before acoustic noise suppression module 310. This is because acoustic noise suppression module 310 works under the assumption that primary signal P(f) only includes the same acoustic background noise and speech as reference signal R(f), albeit with different magnitudes and delays. Wind noise corruption present in one or both of primary signal P(f) and reference signal R(f) can destroy this assumption and, thereby, the ability of acoustic noise suppression module 310 to effectively remove acoustic background noise from primary signal P(f). Therefore, it is important to detect and, potentially, suppress wind noise present in either primary signal P(f) or reference signal R(f) before acoustic noise suppression is performed or, alternatively, forego acoustic noise suppression when wind noise is detected to be present (or above a certain threshold) in either primary signal P(f) or reference signal R(f).

Beyond being used to improve the effectiveness of acoustic noise suppression module 310, wind noise suppression and detection module 305, by detecting and suppressing wind noise in primary signal P(f), more generally improves the perceptual quality and intelligibility of the speech component of primary signal P(f) when played back to a listener.

The following sections describe two different implementations of wind noise detection and suppression module 305. It should be noted that these two implementations are described as being implemented in noise suppression system 300 for illustration purposes only and are not intended to be limiting. Persons skilled in the relevant art(s) will recognize that these implementations of wind noise detection and suppression module 305 can be implemented in a wide number of different multi-microphone devices and noise suppression systems, including noise suppression systems that do not perform acoustic noise suppression. For example, these implementations can be used in a wireless communication device such as a cellular telephone, a PDA, a tablet computer, a non-wireless communication device, a Bluetooth® headset, a hearing aid, a personal recorder, a video recorder, and a sound pick-up system for public speech or on-stage performances.

III. Dual Channel Wind Noise Detection and Suppression

Figure 4:
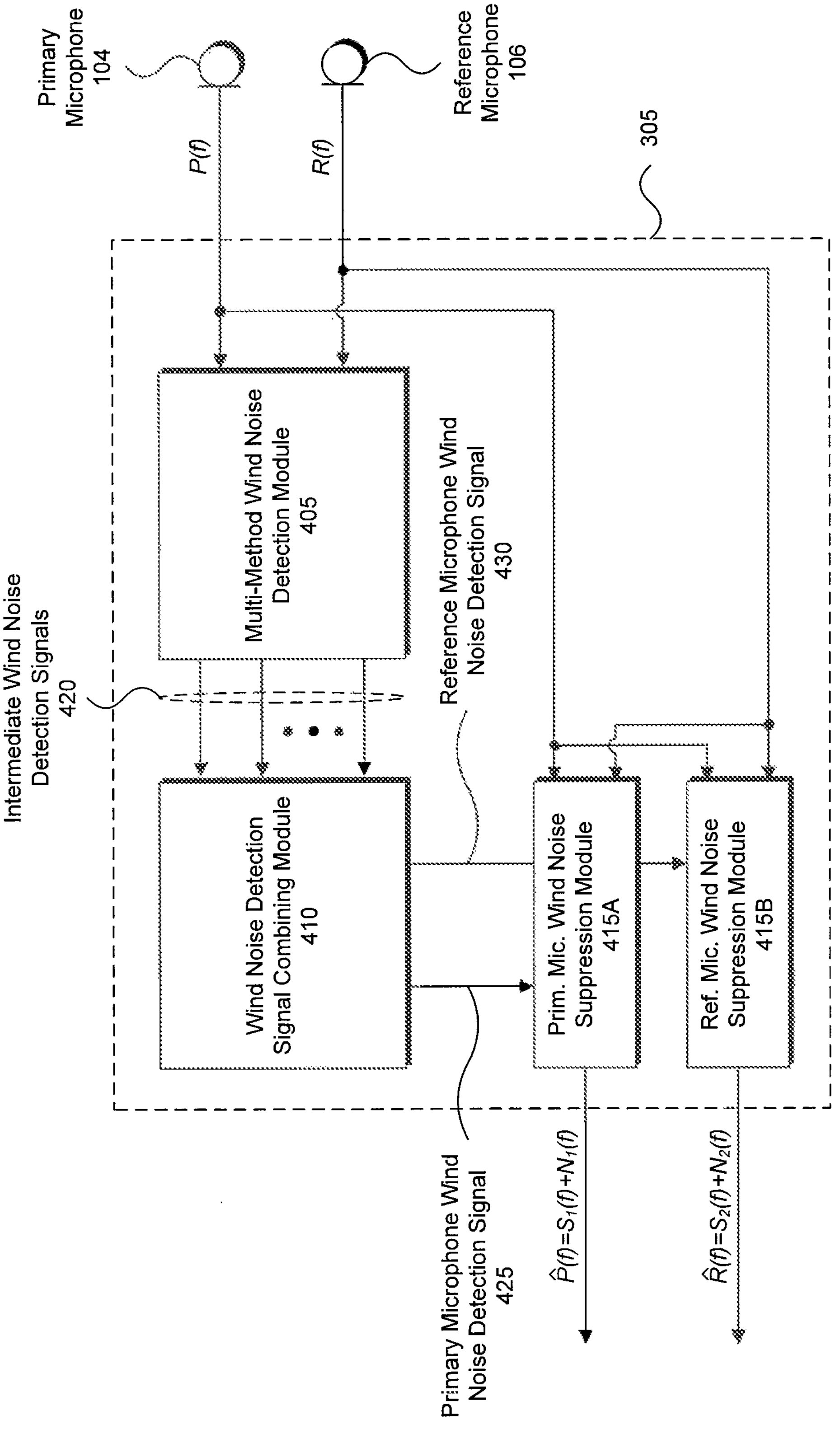
FIG. 4 illustrates a block diagram of an example multi-microphone wind noise detection and suppression module in accordance with embodiments of present invention.

FIG. 4 illustrates a first implementation of wind noise detection and suppression module 305 in accordance with embodiments of the present invention. In general, wind noise detection and suppression module 305 is configured to detect and suppress wind noise in both microphone signals. More specifically, wind noise detection and suppression module 305 is configured to detect and suppress wind noise in primary signal P(f) and in reference signal R(f). Although primary signal P(f) and reference signal R(f) are denoted as being in the frequency domain, wind noise detection and suppression is performed on a frame-by-frame basis, where a frame includes a set of consecutive samples taken from the signals in the time domain. Once taken, however, these samples can be processed by wind noise detection and suppression module 305 in either the time domain and/or can be transformed into the frequency domain for processing. As illustrated in FIG. 4, wind noise detection and suppression module 305 includes a multi-method wind noise detection module 405, a wind noise detection signal combining module 410, a primary microphone wind noise suppression module 415A, and a reference microphone wind noise suppression module 415B.

In operation, primary signal P(f) and reference signal R(f) are first processed by multi-method wind noise detection module 405 on a frame-by-frame basis. In general, multi-method wind noise detection module 405 is configured to detect the presence or absence of wind noise in primary signal P(f) using two or more wind noise detection methods and to detect the presence or absence of wind noise in reference signal R(f) using two or more wind noise detection methods. Each wind noise detection method produces a wind noise detection signal that indicates whether wind noise is present or absent. These detection signals are labeled as intermediate wind noise detection signals 420 in FIG. 4 and are provided as output from multi-method wind noise detection module 405.

In an embodiment, one or more of intermediate wind noise detection signals 420 represent hard decisions that simply indicate whether wind noise is present or absent in primary signal P(f) or reference signal R(f). In other words, these hard decisions do not indicate how much wind noise there is or the likelihood that wind noise is present or absent. In another embodiment, one or more of intermediate wind noise detection signals 420 represent soft decisions that indicate how much wind noise there is or the likelihood that wind noise is present or absent in primary signal P(f) or reference signal R(f).

In yet another embodiment, one or more of intermediate wind noise detection signals 420, corresponding to primary signal P(f), are generated based on both primary signal P(f) and reference signal R(f). In other words, the joint information contained in primary signal P(f) and reference signal R(f) is used to determine whether wind noise is present or absent in primary signal P(f). In another embodiment, one or more of intermediate wind noise detection signals 420, corresponding to reference signal R(f), are generated based on both primary signal P(f) and reference signal R(f).

After intermediate wind noise detection signals 420 are generated, wind noise detection signal combining module 410 is configured to combine them, in some logical manner, to provide primary microphone wind noise detection signal 425 and reference microphone wind noise detection signal 430. Primary microphone wind noise detection signal 425 indicates whether wind noise is present or absent in primary signal P(f), and reference microphone wind noise detection signal 430 indicates whether wind noise is present or absent in reference signal R(f). By combining intermediate wind noise detection signals 420, primary microphone wind noise detection signal 425 and reference microphone wind noise detection signal 430 can more precisely or more accurately indicate whether wind noise is present or absent in primary signal P(f) and reference signal R(f) than any of intermediate wind noise detection signals 420 taken individually.

In an embodiment, wind noise detection signal combining module 410 performs a logical "AND" operation to combine intermediate wind noise detection signals 420 that correspond to primary signal P(f). In this embodiment, primary microphone wind noise detection signal 425 indicates wind noise is present in primary signal P(f) only if each intermediate wind noise detection signal 420, corresponding to primary signal P(f), indicates that wind noise is present or above some threshold value. Otherwise, primary microphone wind noise detection signal 425 indicates wind noise is not present in primary signal P(f). This same scheme can be used to determine reference microphone wind noise detection signal 430 using intermediate wind noise detection signals 420 that correspond to reference signal R(f).

In another embodiment, wind noise detection signal combining module 410 performs a majority vote operation and indicates, through primary microphone wind noise detection signal 425, that wind noise is present in primary signal P(f) if a majority of intermediate wind noise detection signals 420, corresponding to primary signal P(f), indicate wind noise is present or above some threshold value. This same scheme can be used to determine reference microphone wind noise detection signal 430 using intermediate wind noise detection signals 420 that correspond to reference signal R(f).

After wind noise detection signals 425 and 430 have been generated, primary wind noise suppression module 415A and reference wind noise suppression module 415B perform wind noise suppression. More specifically, primary microphone wind noise suppression module 415A performs wind noise suppression on the frame of samples of primary signal P(f) for which wind noise detection took place, and reference wind noise suppression module 415B performs wind noise suppression on the frame of samples of reference signal R(f) for which wind noise detection took place. Wind noise suppression modules 415A and 415B are described further below in regard to FIGS. 7A and 7B, respectively.

Figure 5:
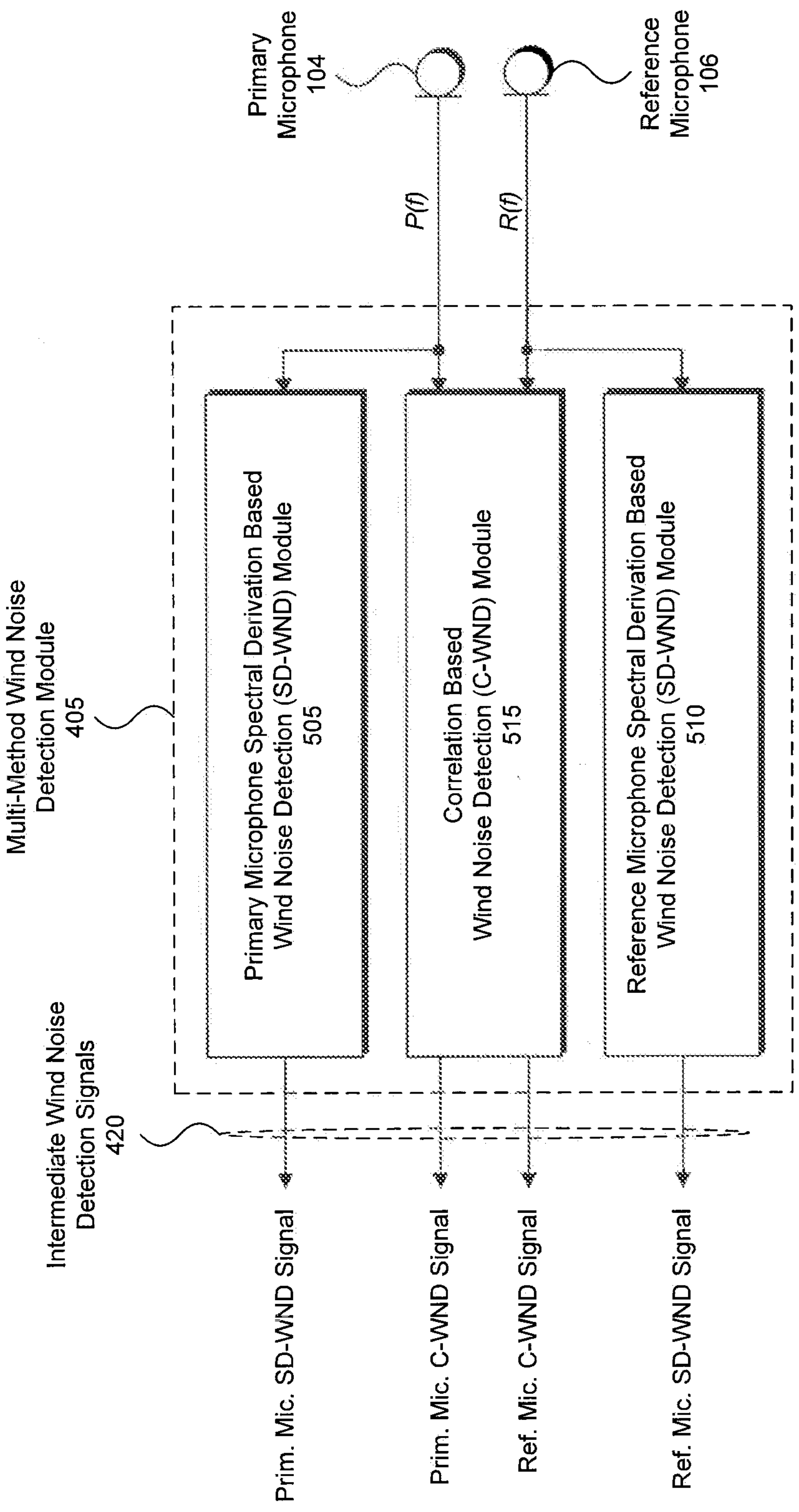
FIG. 5 illustrates a block diagram of an example multi-method wind noise detection module in accordance with embodiments of present invention.

FIG. 5 illustrates an exemplary block diagram of multi-method wind noise detection module 405 in accordance with embodiments of present invention. As illustrated in FIG. 5, multi-method wind noise detection module 405 includes a primary microphone spectral derivation based wind noise detection (SD-WND) module 505, a reference microphone SD-WND module 510, and a correlation based wind noise detection (C-WND) module 515. These modules each perform wind noise detection on a frame-by-frame basis of primary signal P(f) and/or reference signal R(f) and provide an intermediate wind noise detection signal 420 as output that indicates whether wind noise is present or absent in a frame currently being analyzed.

Turning now to the description of SD-WND module 505, it can be shown that the expected spectrum of wind noise has an envelope that decays in a roughly linear fashion with frequency. SD-WND module 505 is configured to exploit this characteristic of wind noise to detect its presence or absence in primary signal P(f). More specifically, SD-WND module 505 is configured to compare the spectrum of a frame of primary signal P(f) with an expected wind noise spectrum having the characteristics noted above (i.e., a spectrum with a magnitude that decreases with frequency and an overall spectral shape that is close to linear). If a difference in the spectrums is greater than a certain threshold, SD-WND module 505 determines that wind noise is absent in primary signal P(f). Otherwise, SD-WND module 505 determines that wind noise is present in primary signal P(f).

In one embodiment, SD-WND module 505 is configured to compare the magnitude or energy of certain frequencies of a frame of primary signal P(f) to corresponding magnitudes or energies of an expected wind noise spectrum. For example, because wind noise is often concentrated in the lower frequency range of speech (e.g., <2250 Hz), SD-WND module 505 can compare the magnitude or energies of only those frequencies of primary signal P(f), within the lower frequency range of speech, to corresponding magnitudes or energies of the expected wind noise spectrum. If a difference in magnitude or energy between the spectrums is greater than a certain threshold, then SD-WND module 505 determines that wind noise is absent in primary signal P(f). Otherwise, SD-WND module 505 determines that wind noise is present in primary signal P(f). Primary microphone SD-WND module 505 provides, as output, primary microphone SD-WND signal that indicates whether wind noise is present or absent in the frame of primary signal P(f).

SD-WND module 510 is configured to operate in a similar manner as described above in regard to SD-WND module 505. However, SD-WND module 510 is configured to detect the presence or absence of wind noise in a frame of reference signal R(f). SD-WND module 510 provides, as output, reference microphone SD-WND signal that indicates whether wind noise is present or absent in the frame of samples of reference signal R(f).

It should be noted that spectral derivation based wind noise detection is a single channel method and is applied on primary signal P(f) and reference signal R(f) separately (i.e., without using the information contained in the other signal). In addition, it should be noted that the thresholds used by SD-WND modules 505 and 510, to determine whether wind noise is present or absent in primary signal P(f) and reference signal R(f), can be different in value.

Turning now to the description of C-WND module 515, the following three facts are exploited by C-WND module 515 to detect whether wind noise is present or absent in primary signal P(f) and reference signal R(f): (1) wind noise typically does not correlate well with acoustic sounds (e.g., speech or background noise); (2) acoustic sounds picked up by a first microphone (e.g., primary microphone 104 illustrated in FIG. 1) typically will correlate well with acoustic sounds picked up by a second microphone that is located in the same general area as the first microphone (e.g., reference microphone 106 illustrated in FIG. 2); and (3) for voiced speech, speech in one portion of a signal picked up by a microphone typically will correlate well with speech in another portion of the same signal one pitch period earlier. In general, voiced speech is nearly periodic and the period of voiced speech at any given moment is referred to as the pitch period. Thus, a frame of samples of a signal containing voiced speech typically correlates well with a similarly sized frame of samples of the same signal from one pitch period earlier. Voiced speech can be generated, for example, by the vocal tract of a speaker when the speaker sounds out a vowel.

Using the three facts noted above, C-WND module 515 detects whether wind noise is present or absent in primary signal P(f) and reference signal R(f), on a frame-by-frame basis, by examining the relationship between: (i) the maximum normalized correlation of primary signal P(f) in an estimated pitch period range; (ii) the maximum normalized correlation of reference signal R(f) in an estimated pitch period range; and (iii) the cross-channel normalized correlation between primary signal P(f) and reference signal R(f).

In one embodiment, if all three of these correlation values are above some defined threshold, it is assumed that primary signal P(f) and reference signal R(f) include voiced speech and wind noise is not present in either primary signal P(f) or reference signal R(f).

In another embodiment, if the cross-channel correlation value in (iii) is above the defined threshold and the same-channel correlation values in (i) and (ii) are below the defined threshold, it is assumed that primary signal P(f) and reference signal R(f) include unvoiced speech and/or background noise and wind noise is not present in either primary signal P(f) or reference signal R(f).

In yet another embodiment, if one of the two same-channel correlation values determined in (i) and (ii) is above the defined threshold and the other is below the defined threshold, and the cross-channel correlation value in (iii) is also below the defined threshold, then it is assumed that wind noise is present in the signal with the same-channel correlation value below the defined threshold and that wind noise is not present in the signal with the same-channel correlation value above the defined threshold (or at least to a much less extent).

It should be noted that different defined thresholds can be used for comparison against each correlation value. It should be further noted that the relative differences, between the three correlation values, can be further used to detect whether wind noise is present or absent in primary signal P(f) and reference signal R(f). For example, in addition to requiring all three correlation values be above some defined threshold in order to assume that wind noise is not present in either primary signal P(f) or reference signal R(f), it can be further required that the relative difference in value between one or more of the correlation values be within some defined range. In addition, it should be further noted that the three correlation values can be non-normalized in other embodiments.

C-WND module 515 provides, as output, two intermediate wind noise detection signals 420 based on the relationship between the correlation values as outlined above. More specifically, C-WND module 515 provides a primary microphone C-WND signal and a reference microphone C-WND signal, as output, to respectively indicate whether wind noise is present or absent in primary signal P(f) and reference signal R(f).

Figure 6:
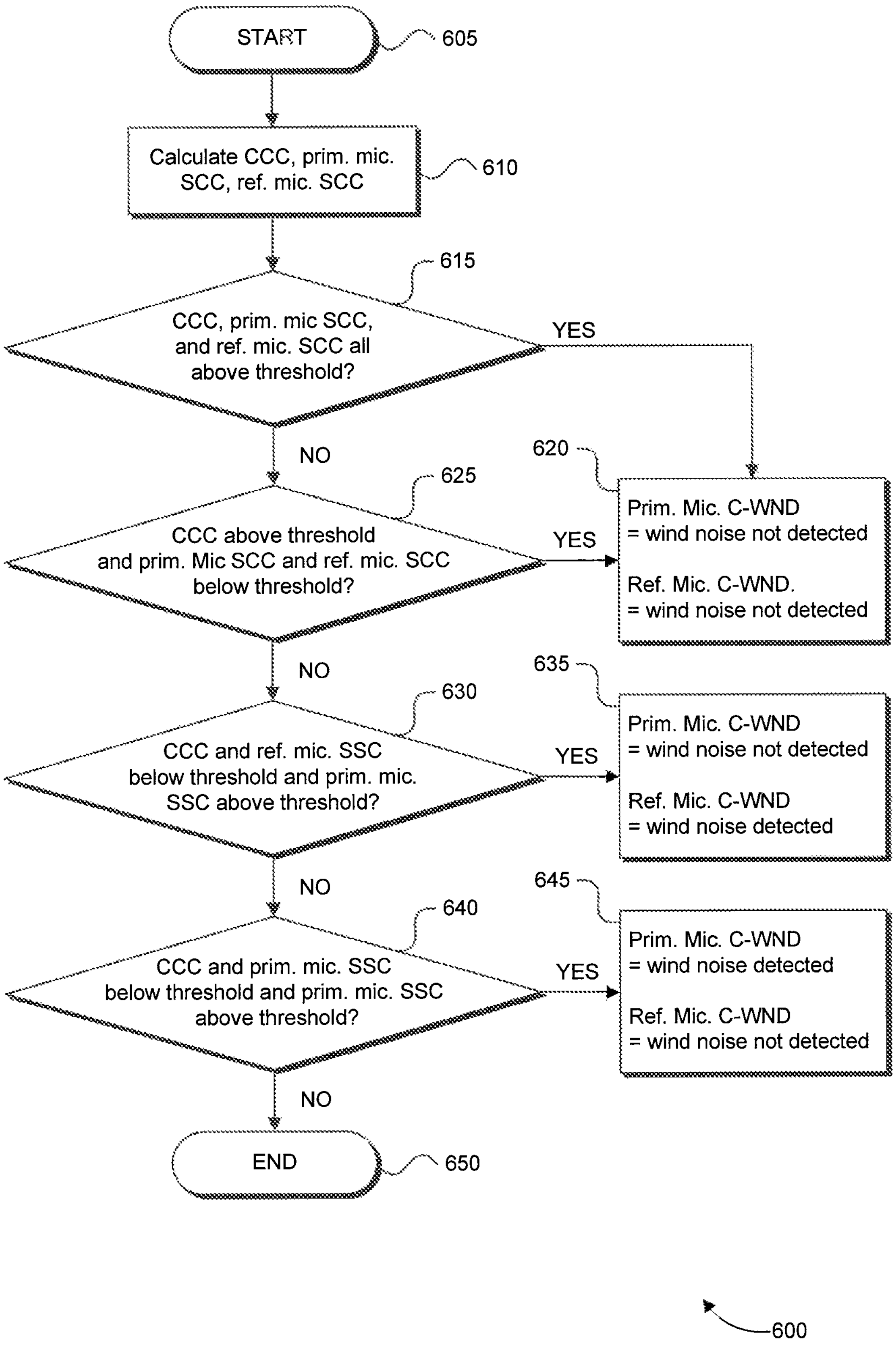
FIG. 6 illustrates a flowchart of a method for correlation based wind noise detection in accordance with embodiments of the present invention.

FIG. 6 depicts a flowchart 600 of a method for correlation based wind noise detection in accordance with embodiments of the present invention. The method of flowchart 600 can be implemented by C-WND module 515 as described above in reference to FIG. 5. However, it should be noted that the method can be implemented by other systems and components as well. It should be further noted that some of the steps of flowchart 600 do not have to occur in the order shown in FIG. 6.

The method of flowchart 600 begins at step 605 and transitions to step 610. At step 610, the maximum normalized correlation of primary signal P(f) in the pitch period range is calculated (labeled as prim. mic. single channel correlation (SCC) in FIG. 6), the maximum normalized correlation of reference signal R(f) in the pitch period range is calculated (labeled as ref. mic. SCC in FIG. 6), and the cross-channel normalized correlation between primary signal P(f) and reference signal R(f) is calculated (labeled as cross-channel correlation (CCC) in FIG. 6).

During decision step 615, if the three calculated correlation values (i.e., CCC, prim. mic. SCC, and ref. mic. SCC) are all above a defined threshold, output signal primary microphone C-WND is set to a value that indicates wind noise is not present in primary signal P(f) and output signal reference microphone C-WND is set to a value that indicates wind noise is not present in reference signal R(f) as shown in step 620. In general, if the three calculated correlation values are all above the defined threshold, it is assumed that primary signal P(f) and reference signal R(f) include voiced speech and wind noise is not present in either primary signal P(f) or reference signal R(f). On the other hand, if the three conditions in step 615 are not all true, flowchart 600 proceeds to step 625.

During decision step 625, if CCC is above the defined threshold and primary microphone SCC and reference microphone SCC are below the defined threshold, primary microphone C-WND signal is set to a value that indicates wind noise is not present in primary signal P(f) and reference microphone C-WND signal is set to a value that indicates wind noise is not present in reference signal R(t) as shown in step 620. In general, if CCC is above the defined threshold and primary microphone SCC and reference microphone SCC are below the defined threshold, it is assumed that primary signal P(f) and reference signal R(f) include unvoiced speech and/or background noise and wind noise is not present in either primary signal P(f) or reference signal R(f). On the other hand, if the three conditions in step 625 are not all true, flowchart 600 proceeds to step 630.

During decision step 630, if CCC and reference microphone SCC are below the defined threshold and primary microphone SCC is above the defined threshold, primary microphone C-WND signal is set to a value that indicates wind noise is not present in primary signal P(f) and reference microphone C-WND signal is set to a value that indicates wind noise is present in reference signal R(f) as shown in step 635. On the other hand, if the three conditions in step 630 are not all true, flowchart 600 proceeds to step 640.

During decision step 640, if CCC and primary microphone SCC are below the defined threshold and reference microphone SCC is above the defined threshold, primary microphone C-WND signal is set to a value that indicates wind noise is present in primary signal P(f) and reference microphone C-WND signal is set to a value that indicates wind noise is not present in reference signal R(f) as shown in step 645. On the other hand, if the three conditions in step 640 are not all true, flowchart 600 proceeds to step 650.

At step 650, flowchart 600 ends and if primary microphone C-WND signal and reference microphone C-WND signal are not set (i.e., they do not indicate, either way, whether wind noise is present or not) then the subsequent processing logic can deal with the indeterminate values of primary microphone C-WND signal and reference microphone C-WND signal. In another embodiment, rather than simply ending flowchart 600 at step 650 and leaving the values of primary microphone C-WND signal and reference microphone C-WND undetermined, these two values can be set to a default value.

It should be noted, in regard to flowchart 600, that different defined thresholds can be used for comparison against each correlation value (i.e., CCC, prim. mic. SCC, and ref. mic. SCC). It should be further noted, in regard to flowchart 600, that the relative differences between the three correlation values can be further used to detect whether wind noise is present or absent in primary signal P(f) and reference signal R(f). For example, in addition to requiring all three correlation values be above some defined threshold in step 615 in order to assume that wind noise is not present in either primary signal P(f) or reference signal R(f), it can be further required that the relative difference in value between one or more of the correlation values be within some defined range. In addition, it should be further noted that the three correlation values calculated in step 610 can be non-normalized in other embodiments.

Figure 7A:
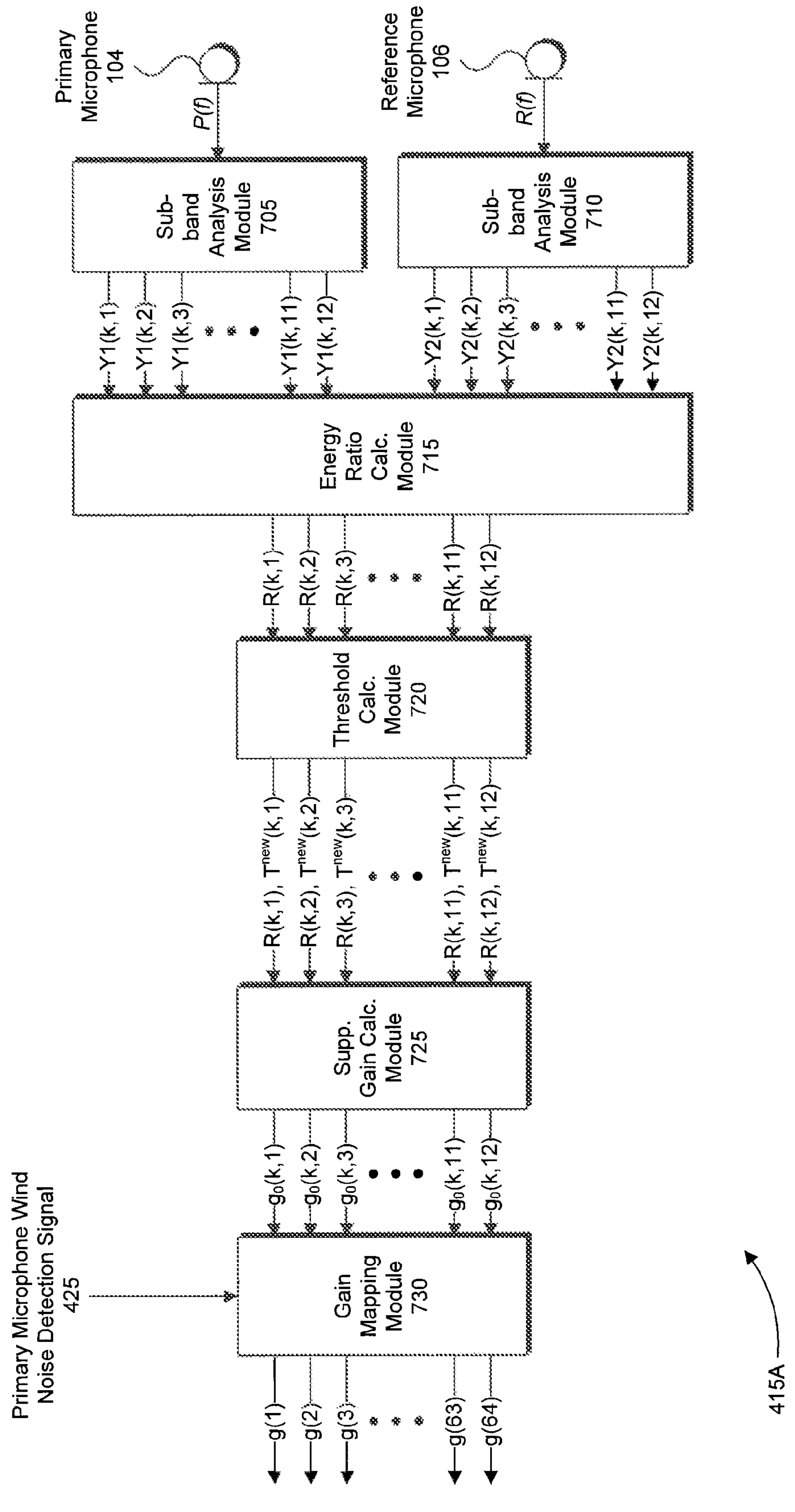
FIG. 7A illustrates an example primary microphone wind noise suppression module in accordance with embodiments of present invention.

Referring now to FIG. 7A, an example implementation of primary microphone wind noise suppression module 415A is illustrated in accordance with embodiments of the present invention. Primary microphone wind noise suppression module 415A is configured to suppress wind noise in primary signal P(f) based on differences in energy between corresponding sub-bands of primary P(f) and reference signal R(f).

As discussed above, wind noise picked up by primary microphone 104 or reference microphone 106 often will not be picked up (or at least not to the same extent) by the other microphone because air turbulence caused by wind is usually a fairly local event. Therefore, a difference in energy between corresponding sub-bands of primary signal P(f) and reference signal R(f) can provide a good indication as to how much wind noise, if any, is present in each signal and, thereby, how much wind noise to suppress in each signal. However, in some instances, a difference in energy between corresponding sub-bands of primary signal P(f) and reference signal R(f) can be misrepresentative of the actual amount of wind noise present in each signal. Therefore, primary microphone wind noise suppression module 415A is further configured to utilize primary microphone wind noise detection signal 425 to improve suppression results, the generation of which was described above in regard to FIGS. 4, 5, and 6.

As illustrated in FIG. 7A, primary microphone wind noise suppression module 415A specifically includes a sub-band analysis module 705, a sub-band analysis module 710, an energy ratio calculation module 715, a threshold calculation module 720, a suppression gain calculation module 725, and a gain mapping module 730.

In operation, sub-band analysis module 705 is configured to process primary signal P(f) on a frame-by-frame basis, where a frame includes a set of consecutive samples taken from primary signal P(f) in the time domain. In one embodiment, sub-band analysis module 705 is configured to receive each frame of primary signal P(f) already transformed into the frequency domain. In another embodiment, sub-band analysis module 705 is configured to receive each frame of primary signal P(f) in the time domain and is configured to calculate the discrete Fourier transform (DFT) of each frame to transform the frames into the frequency domain. Sub-band analysis module 705 can calculate the DFT using, for example, the Fast Fourier Transform (FFT). In general, the resulting frequency domain signal describes the magnitudes and phases of component cosine waves (also referred to as component frequencies) that make up the time domain frame, where each component cosine wave corresponds to a particular frequency between DC and one-half the sampling rate used to obtain the samples of the time domain frame.

For example, and in one embodiment, each time domain frame of primary signal P(f) includes 128 samples and is transformed into the frequency domain using a 128-point DFT by sub-band analysis module 705 or some other module not shown. The 128-point DFT provides 64 values that represent the magnitudes of the component cosine waves that make up the time domain frame. In another embodiment, each time domain frame of primary signal P(f) includes N samples and is transformed into the frequency domain using an M-point DFT by sub-band analysis module 705 or some other module not shown, where N and M are integer numbers and M is greater than or equal to N. When M is larger than N, the N samples of primary signal P(f) can be padded with M-N zeroes.

Once the magnitudes of the component cosine waves are obtained for a frame of primary signal P(f), sub-band analysis module 705 is configured to group the cosine wave components into sub-bands, where a sub-band can include one or more cosine wave components. In one embodiment, sub-band analysis module 705 is configured to group the cosine wave components into sub-bands based on the Bark frequency scale. As is well known, the Bark frequency scale ranges from 1 to 24 Barks and each Bark corresponds to one of the first 24 critical bands of hearing.

Table 1 below provides an example grouping of 62 component cosine waves (i.e., component cosine waves 3 through 64) into 16 sub-bands based on the Bark frequency scale. Each of the 62 component cosine waves has a corresponding magnitude obtained using a 128-point DFT (the first two component cosine waves 1-2, and their corresponding magnitudes, are ignored). The 128-point DFT is specifically calculated over a frame of 128 time-domain samples of primary signal P(f) obtained at a sampling rate of 8000 Hz.

TABLE 1

Example Sub-band Groupings

| Sub-band # | component cosine wave # |
|---|---|
| 1 | 3-4 |
| 2 | 5-6 |
| 3 | 7-8 |
| 4 | 9-10 |
| 5 | 11-12 |
| 6 | 13-14 |
| 7 | 15-17 |
| 8 | 18-20 |
| 9 | 21-23 |
| 10 | 24-27 |
| 11 | 28-31 |
| 12 | 32-36 |
| 13 | 37-42 |
| 14 | 43-49 |
| 15 | 50-56 |
| 16 | 57-64 |

In one embodiment, the cosine wave components are grouped into each sub-band by adding their corresponding squared magnitudes together. For example, the $3^{rd}$ and $4^{th}$ cosine wave components are grouped into the first sub-band, as indicated by table 1 above, by adding their corresponding squared magnitudes together. The resulting sum represents an estimated energy of the first sub-band. Extending the exemplary sub-band grouping provided in table 1 to the illustration of FIG. 7A, sub-band analysis module 705 provides the resulting squared sum of the $3^{rd}$ and $4^{th}$ cosine wave component magnitudes as output Y1(k,1), where Y1(k,i) is a two dimensional array indexed by frame number (k) and sub-band number (i). Thus, Y1(k,1) represents the estimated energy of the first sub-band in the $k^{th}$ frame of primary signal P(f), Y1(k,2) represents the estimated energy of the second sub-band in the $k^{th}$ frame of primary signal P(f), etc.

It should be noted that table 1 is for illustration purposes only and is not intended to be limiting. Persons skilled in the relevant art(s) will recognize that other groupings can be used, for example, based on different sampling rates and DFT sizes. It should be further noted that the cosine wave components can be grouped using other methods that provide a reasonable estimate of the energy of the sub-band to which they belong.

In one embodiment, sub-band analysis module 705 is configured to provide estimated sub-band energies for sub-bands corresponding only to a lower frequency range of speech. For example, and as shown in FIG. 7A, sub-band analysis module 705 can be configured to provide estimated sub-band energies for only sub-bands 1-12; estimated sub-band energies for sub-bands 13-16 are not calculated or are not provided as output. As discussed above, the expected spectrum of wind noise has an envelope that decays in a roughly linear fashion with frequency and is often concentrated in the lower frequency range of speech (e.g., <2250 Hz). Therefore, upper sub-bands that correspond to higher frequencies of speech (e.g., >2250 Hz) can be ignored because wind noise generally does not corrupt those frequencies.

Sub-band analysis module 710 is configured to provide estimated energies for sub-bands corresponding to frames in reference signal R(f) in a similar manner as sub-band analysis module 705 described above. The estimated energies are provided as output in a two dimensional array Y2(k,i) indexed by frame number (k) and sub-band number (i).

Energy ratio calculation module 715 is configured to determine a difference in energy between corresponding sub-bands of primary signal P(f) and reference signal R(f). In one embodiment, energy ratio calculation module 715 is configured to divide the sub-band energies of primary signal P(f), provided by sub-band analysis module 705, by corresponding sub-band energies of reference signal R(f), provided by sub-band analysis module 710, to determine differences in energy. For example, energy ratio calculation module 715 is configured to divide the sub-band energy Y1(k,1) by the sub-band energy Y2(k,1) and provide the resulting quotient as output R(k,1), where R(k,i) is a two dimensional array indexed by frame number (k) and sub-band number (i). Thus, R(k,1) represents the difference in energy between the first sub-band of the $k^{th}$ frame of primary signal P(f) and the first sub-band of the $k^{th}$ frame of reference signal R(f).

In another embodiment, energy ratio calculation module 715 is configured to subtract the sub-band energies of primary signal P(f), provided by sub-band analysis module 705, from corresponding sub-band energies of reference signal R(f), provided by sub-band analysis module 710, to determine differences in energy. The resulting values of each subtraction are provided as output R(k,i), in this embodiment, energy ratio calculation module 714 may be more aptly referred to as an energy difference calculation module 714.

Threshold calculation module 720 is configured to calculate threshold values for the sub-bands of primary signal P(f) that are to be used to determine how much wind noise suppression to apply to a particular sub-band. In one embodiment, threshold calculation module 720 is configured to calculate threshold values for the sub-bands of primary signal P(f) based on the differences in energy between corresponding sub-bands of primary signal P(f) and reference signal R(f), represented by two dimensional array R(k,i), and based on previously calculated threshold values. For example, and in one embodiment, threshold calculation module 720 is configured to calculate a threshold value for the $i^{th}$ sub-band of the $k^{th}$ frame of primary signal P(f), represented by $T^{new}(k,i)$, according to the following equations:

$$T^{new}(k,i)=\alpha\times T^{old}(k,i)+(1-\alpha)\times R(k,i)$$

$$T^{old}(k+1,i)=T^{new}(k,i)$$

where $T^{old}(k,i)$ represents the threshold value calculated for the $i^{th}$ sub-band of the previous frame (i.e., frame k−1) and $\alpha$ is a smoothing factor with a value between 0 and 1. As illustrated in FIG. 7A, threshold calculation module 720 provides, as output, the calculated threshold values ($T^{new}(k,i)$) and the differences in energy between corresponding sub-bands of primary signal P(f) and reference signal R(f)(R(k,i)).

Suppression gain calculation module 725 is configured to determine suppression gains for the sub-bands of primary signal P(f) based on the calculated threshold values (i.e., $T^{new}(k,i)$) and the differences in energy between corresponding sub-bands of primary signal P(f) and reference signal R(f) (i.e., R(k,i)). In one embodiment, suppression gain calculation module 725 multiplies each calculated threshold value for the $k^{th}$ frame of primary signal P(f), represented by $T^{new}(k,i)$, by two constant values: a speech constant with a value 's', and a wind noise constant with a value 'w'.

Figure 8:
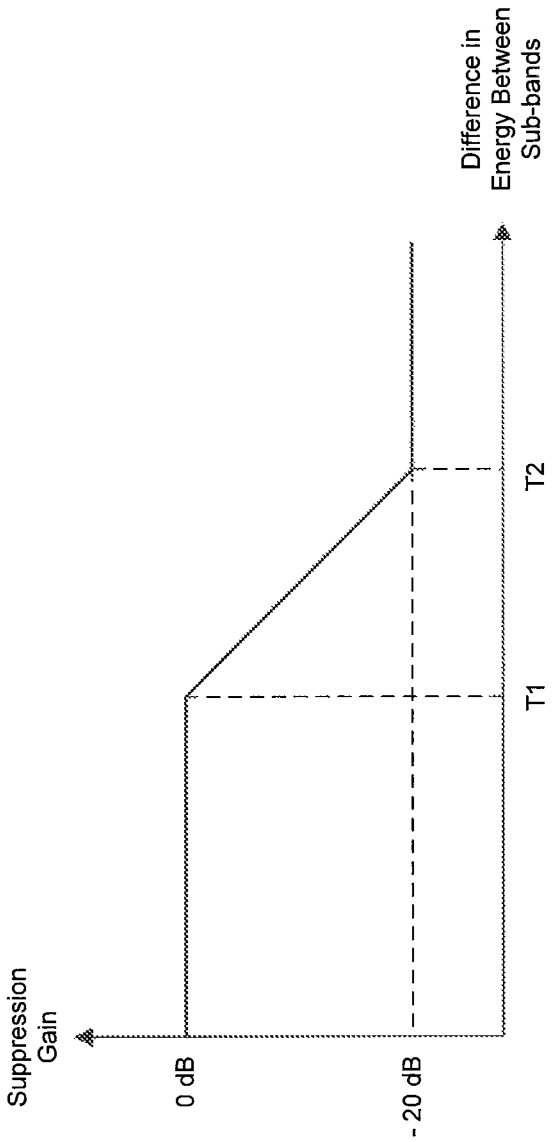
FIG. 8 illustrates an example suppression gain versus difference in energy plot in accordance with embodiments of present invention.

For example, for the first sub-band of the $k^{th}$ frame of primary signal P(f), the threshold value represented by $T^{new}(k,1)$ is multiplied by the speech constant 's', to obtain a speech threshold T1, and by the wind noise constant 'w', to obtain a wind noise threshold T2. Suppression gain calculation module 725 is then configured to use these two threshold values, T1 and T2, to construct a suppression gain function. FIG. 8 illustrates one example plot 800 of a suppression gain function constructed using threshold values T1 and T2. As illustrated in FIG. 8, plot 800 is a plot of suppression gain versus difference in energy between sub-bands and is used by suppression gain calculation module 725 to determine a suppression gain for a sub-band of primary signal P(f).

In the instant example, plot 800 was constructed using threshold values T1 and T2 calculated for the first sub-band of the $k^{th}$ frame of primary signal P(f). Therefore, plot 800 (and the function it represents) would be used to determine a suppression gain for the first sub-band of the $k^{th}$ frame of primary signal P(f). More specifically, suppression gain calculation module 725 would use the difference in energy between the first sub-band of the $k^{th}$ frame of primary signal P(f) and the first sub-band of the $k^{th}$ frame of reference signal R(f), represented by R(k,1), as the independent variable of the function represented by plot 800 to determine a suppression gain.

For example, if the difference in energy represented by R(k,1) is less than T1, the function represented by plot 800 would return a suppression gain of 0 dB. The threshold T1 is referred to as the speech threshold because it is assumed that primary signal P(f) is substantially wind noise free when the calculated difference in energy between corresponding sub-bands of primary signal P(f) and reference signal R(f) is below T1. Therefore, the function represented by plot 800 returns 0 dB (i.e. no suppression), for the first sub-band of primary signal P(f) if the difference in energy represented by R(k,1) is less than T1.

If the difference in energy represented by R(k,1) is greater than T2, the function represented by plot 800 would return a suppression gain of −20 dB. T2 is referred to as the wind noise threshold because it is assumed that primary signal P(f) contains a substantial amount of wind noise when the difference in energy between corresponding sub-bands of primary signal P(f) and reference signal R(f) is greater than T2. Therefore, the function represented by plot 800 returns a large amount of suppression, such as −20 dB, for the first sub-band of primary signal P(f) if the difference in energy represented by R(k,1) is greater than T2.

If the difference in energy represented by R(k,1) is greater than T1 and less than T2, the function represented by plot 800 would return a suppression gain between 0 dB and −20 dB. As specifically illustrated in plot 800, the suppression gain changes from 0 dB to −20 dB as the difference in energy between sub-bands increases from T1 to T2. If the difference in energy represented by R(k,1) falls between T1 and T2 it is assumed that primary signal P(f) contains some wind noise and some speech.

In an embodiment, suppression gain calculation module 725 is configured to smooth the suppression gains determined for each sub-band across adjacent sub-bands and/or frames (or time).

It should be noted that, in FIG. 8, 0 dB and −20 dB are provided by way of example and not limitation. Persons skilled in the relevant art(s) will recognize that other suppression gain values can be used for differences in sub-band energy that fall below T1 or above T2. In addition, it should be noted that the linearly increasing function of suppression gain between T1 and T2 is provided by way of example and not limitation. Persons skilled in the relevant art(s) will recognize that other increasing functions of suppression gain, such as an exponentially increasing function of suppression gain, can be used to describe the suppression gains between T1 and T2.

In general, suppression gain calculation module 725 is configured to construct a suppression gain function that provides: a constant suppression gain of 0 dB for differences in energy that are less than T1; a large, constant amount of suppression (e.g., −20 dB) for differences in energy that are greater than T2; and a suppression amount that increases as the difference in energy between sub-bands increases from T1 to T2.

Referring back to FIG. 7A, suppression gain calculation module 725 provides the calculated suppression gains for each sub-band of primary signal P(f) as output $g_0(k,i)$, where $g_0(k,i)$ is a two dimensional array indexed by frame number (k) and sub-band number (i).

Gain mapping module 730 is configured to map the suppression gains for each sub-band of primary signal P(f) (i.e., $g_0(k,i)$) to the component cosine waves (also referred to as component frequencies) of primary signal P(f). For example, gain mapping module 730 is configured to map the suppression gain for the first sub-band of the $k^{th}$ frame of primary signal P(f), represented by $g_0(k,1)$, to the component cosine waves grouped into the first sub-band. In an embodiment, gain mapping module 730 is configured to map the suppression gain for the first sub-band of the $k^{th}$ frame of primary signal P(f), represented by $g_0(k,1)$, to the component cosine waves grouped into the first sub-band by interpolating between the suppression gain of the first sub-band and the suppression gain of the second sub-band, represented by $g_0(k, 2)$.

In another embodiment, for higher frequency sub-bands in which a suppression gain was not calculated, gain mapping module 730 is configured to set the suppression gain for the component cosine waves belonging to these sub-bands to a value of 0 dB.

In yet another embodiment, gain mapping module 730 is configured to set the suppression gain for each component cosine wave of primary signal P(f) to 0 dB if primary microphone wind noise detection signal 425 indicates that wind noise is not present in primary signal P(f).

Figure 7B:
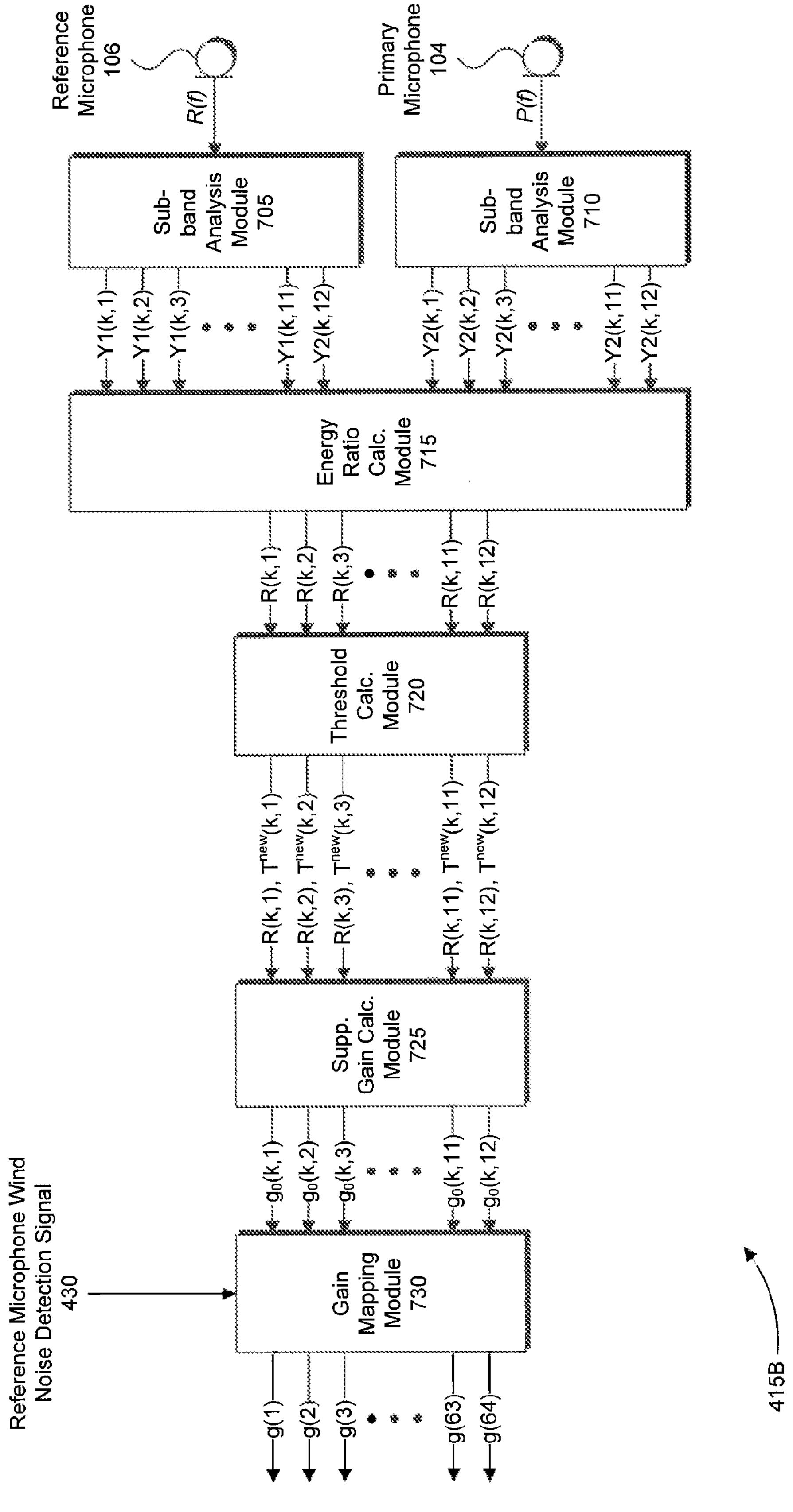
FIG. 7B illustrates an example reference microphone wind noise suppression module in accordance with embodiments of present invention.

Referring now to FIG. 7B, an example implementation of reference microphone wind noise suppression module 415B is illustrated in accordance with embodiments of the present invention. Reference microphone wind noise suppression module 415A is configured to suppress wind noise in reference signal R(f) based on differences in energy between corresponding sub-bands of reference signal R(f) and primary signal P(f) in a similar manner as primary microphone wind noise suppression module 415A described above.

Figure 9:
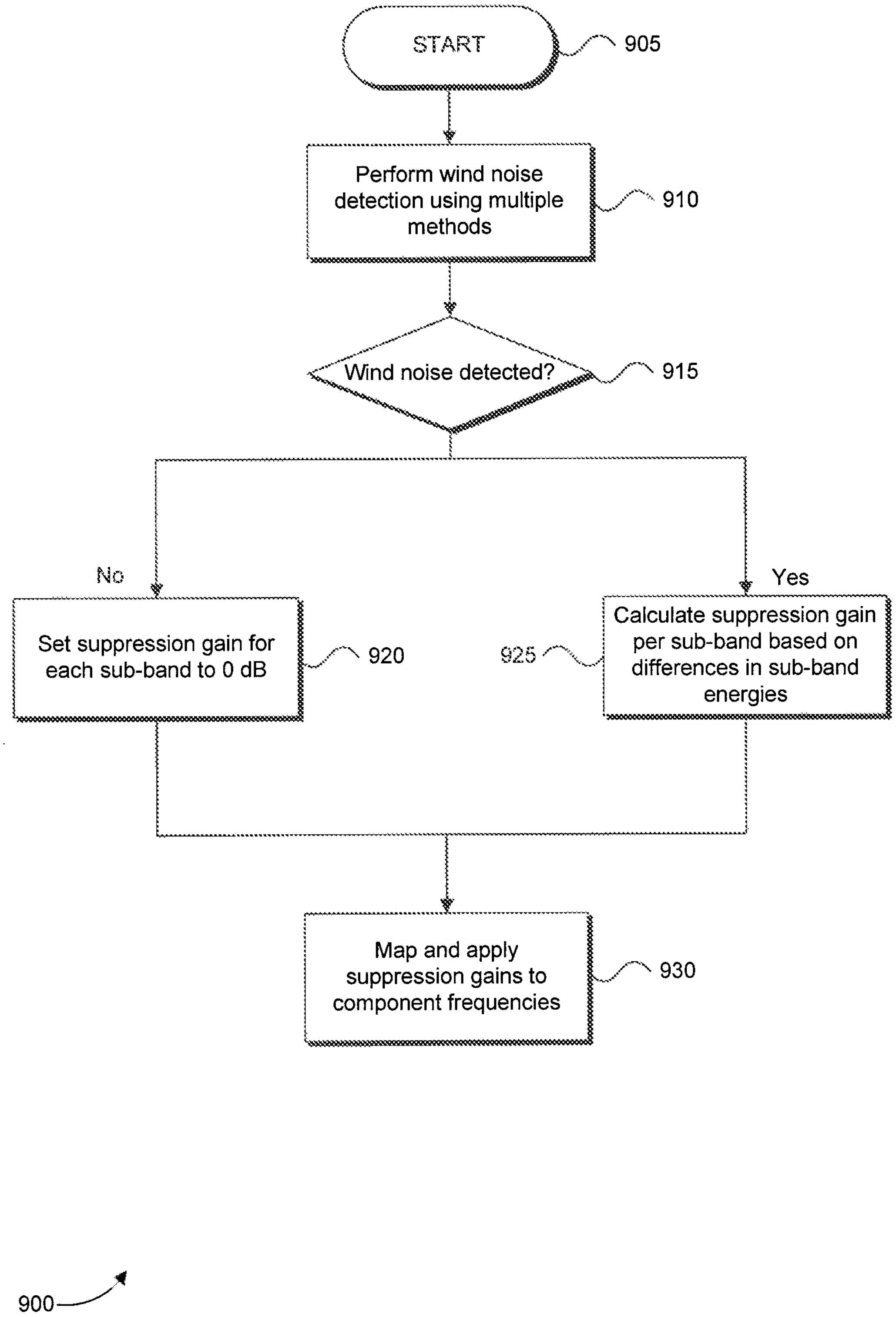
FIG. 9 illustrates a flowchart of an example method for multi-microphone wind noise detection and suppression in accordance with embodiments of present invention.

Referring now to FIG. 9, a flowchart 900 of an example method for multi-microphone wind noise detection and suppression in accordance with embodiments of present invention is illustrated. The method of flowchart 900 can be implemented by wind noise detection and suppression module 305 as described above and illustrated in FIG. 4. However, it should be noted that the method can be implemented by other systems and components as well. It should be further noted that some of the steps of flowchart 900 do not have to occur in the order shown in FIG. 9.

The method of flowchart 900 begins at step 905 and transitions to step 910. At step 910, wind noise detection is performed on primary signal P(f) and reference signal R(f) using multiple methods. More specifically, at step 910 wind noise detection is performed to detect the presence or absence of wind noise in primary signal P(f) using two or more wind noise detection methods and to detect the presence or absence of wind noise in reference signal R(f) using two or more wind noise detection methods. Each wind noise detection method produces a wind noise detection signal that indicates whether wind noise is present or absent. In an embodiment, spectral-deviation based wind noise detection and correlation based wind noise detection are performed to determine if primary signal P(f) or reference signal R(f) contain wind noise. The resulting wind noise detection signals corresponding to primary signal P(f) are combined to produce a single wind noise detection signal for primary signal P(f), and the resulting wind noise detection signals corresponding to reference signal R(f) are combined to produce a single wind noise detection signal for reference signal R(f). Further details regarding wind noise detection using multiple methods were described above in regard to FIGS. 5 and 6 and are incorporated here by reference.

At step 915, based on the combined wind noise detection signals for primary signal P(f) and reference signal R(f), produced at step 910, flowchart 900 proceeds to step 920 or step 925. For example, if the combined wind noise detection signal for primary signal P(f) indicates that wind noise is not present in primary signal P(f), flowchart 900 proceeds to step 920 for primary signal P(f). Otherwise, flowchart 900 proceeds to step 925 for primary signal P(f). Similarly, if the combined wind noise detection signal for reference signal R(f) indicates that wind noise is not present in reference signal R(f), flowchart 900 proceeds to step 920 for reference signal R(f). Otherwise, flowchart 900 proceeds to step 925 for reference signal R(f).

At step 920, suppression gains for sub-bands of primary signal P(f) and/or reference signal R(f) are set to 0 dB (or some other low suppression gain).

At step 925, suppression gains are calculated for the sub-bands of primary signal P(f) and/or reference signal R(f) based on differences in energy between corresponding sub-bands of primary signal P(f) and reference signal R(f). Details regarding the calculation of suppression gains for the sub-bands of primary signal P(f) and/or reference signal R(f) were described above in regard to FIGS. 7A, 7B, and 8 and are incorporated here by reference.

At step 930 the suppression gains for the sub-bands of primary signal P(f) and reference signal R(f) are mapped and applied to the component cosine waves (also referred to as component frequencies) of primary signal P(f) and reference signal R(f). Details regarding the mapping of suppression gains were described above in regard to FIGS. 7A and 7B and are incorporated here by reference.

IV. Dual Channel Wind Noise Detection, Single Channel Wind Noise Suppression

Figure 10:
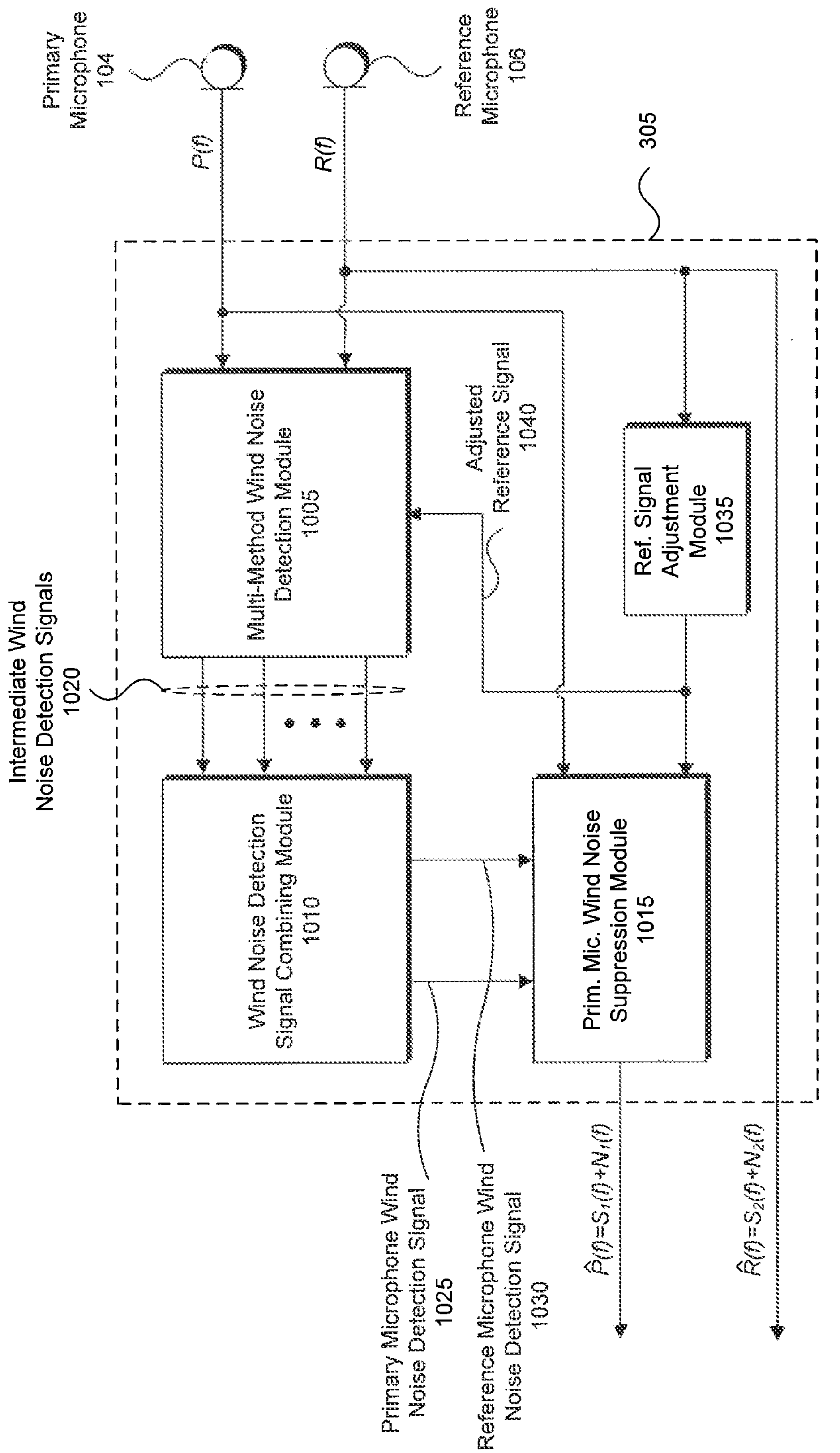
FIG. 10 illustrates a block diagram of another example multi-microphone wind noise detection and suppression module in accordance with embodiments of present invention.

FIG. 10 illustrates a second implementation of wind noise detection and suppression module 305 in accordance with embodiments of the present invention. In general, wind noise detection and suppression module 305, illustrated in FIG. 10, is configured to detect wind noise in both primary signal P(f) and reference signal R(f). However, wind noise detection and suppression module 305 is configured to suppress wind noise in primary signal P(f) and not in reference signal R(f). Although primary signal P(f) and reference signal R(f) are denoted as being in the frequency domain in FIG. 10, wind noise detection and suppression is performed on a frame-by-frame basis, where a frame includes a set of consecutive samples taken from the signals in the time domain. Once taken, however, these samples can be processed by wind noise detection and suppression module 305 in either the time domain and/or can be transformed into the frequency domain for processing. As illustrated in FIG. 10, wind noise detection and suppression module 305 includes a multi-method wind noise detection module 1005, a wind noise detection signal combining module 1010, a primary microphone wind noise suppression module 1015, and a reference signal adjustment module 1035.

In operation, primary signal P(f) and reference signal R(f) are first processed by multi-method wind noise detection module 1005 on a frame-by-frame basis. In general, multi-method wind noise detection module 1005 is configured to detect the presence or absence of wind noise in primary signal P(f) using two or more wind noise detection methods and to detect the presence or absence of wind noise in reference signal R(f) using two or more wind noise detection methods. Each wind noise detection method produces a wind noise detection signal that indicates whether wind noise is present or absent. These detection signals are labeled as intermediate wind noise detection signals 1020 in FIG. 10 and are provided as output from multi-method wind noise detection module 1005.

In an embodiment, one or more of intermediate wind noise detection signals 1020 represent hard decisions that simply indicate whether wind noise is present or absent in primary signal P(f) or reference signal R(f). In other words, these hard decisions do not indicate how much wind noise there is or the likelihood that wind noise is present or absent. In another embodiment, one or more of intermediate wind noise detection signals 1020 represent soft decisions that indicate how much wind noise there is or the likelihood that wind noise is present or absent in primary signal P(f) or reference signal R(f).

In another embodiment, one or more of intermediate wind noise detection signals 1020, corresponding to primary signal P(f), are generated based on both primary signal P(f) and reference signal R(f). In other words, the joint information contained in primary signal P(f) and reference signal R(f) is used to determine whether wind noise is present or absent in primary signal P(f). In yet another embodiment, one or more of intermediate wind noise detection signals 1020, corresponding to reference signal R(f), are generated based on both primary signal P(f) and reference signal R(f).

After intermediate wind noise detection signals 1020 are generated, wind noise detection signal combining module 1010 is configured to combine them, in some logical manner, to provide primary microphone wind noise detection signal 1025 and reference microphone wind noise detection signal 1030. Primary microphone wind noise detection signal 1025 indicates whether wind noise is present or absent in primary signal P(f), and reference microphone wind noise detection signal 1030 indicates whether wind noise is present or absent in reference signal R(f). By combining intermediate wind noise detection signals 1020, primary microphone wind noise detection signal 1025 and reference microphone wind noise detection signal 1030 can more precisely or more accurately indicate whether wind noise is present or absent in primary signal P(f) and reference signal R(f) than any of intermediate wind noise detection signals 1020 taken individually.

In an embodiment, wind noise detection signal combining module 1010 performs a logical "AND" operation to combine intermediate wind noise detection signals 1020 that correspond to primary signal P(f). In this embodiment, primary microphone wind noise detection signal 1025 indicates wind noise is present in primary signal P(f) only if each intermediate wind noise detection signal 1020, corresponding to primary signal P(f), indicates that wind noise is present or above some threshold value. Otherwise, primary microphone wind noise detection signal 1025 indicates wind noise is not present in primary signal P(f). This same scheme can be used to determine reference microphone wind noise detection signal 1030 using intermediate wind noise detection signals 1020 that correspond to reference signal R(f).

In another embodiment, wind noise detection signal combining module 1010 performs a majority vote operation and indicates, through primary microphone wind noise detection signal 1025, that wind noise is present in primary signal P(f) if a majority of intermediate wind noise detection signals 1020, corresponding to primary signal P(f), indicate wind noise is present or above some threshold value. This same scheme can be used to determine reference microphone wind noise detection signal 1030 using intermediate wind noise detection signals 1020 that correspond to reference signal R(f).

After wind noise detection signals 1025 and 1030 have been generated, primary microphone wind noise suppression module 1015 is configured to perform wind noise suppression on primary signal P(f). More specifically, primary microphone wind noise suppression module 1015 performs wind noise suppression on the frame of samples of primary signal P(f) for which wind noise detection took place.

In general, when wind noise is present or above some threshold in the frame of primary signal P(f), as indicated by primary microphone wind noise detection signal 1020, and wind noise is absent or below some threshold in the corresponding frame of reference signal R(f), as indicated by reference microphone wind noise detection signal 1030, primary microphone wind noise suppression module 1015 is configured to replace (at least a portion of) the wind noise corrupted frame of primary signal P(f) with (at least a portion of) the comparatively cleaner frame of reference signal R(f). The "at least a portion of" above can mean some portion of the time domain samples or some portion of the DFT coefficients that are corrupted by wind noise more than the remaining portions. The same applies to this term when used in the description that follows.

To maintain consistent speech characteristics of primary signal P(f), reference signal adjustment module 1035 is configured to adjust one or more of the delay, gain, spectral shape, and background noise level of reference signal R(f) to match those of primary signal P(f) before portions of primary signal P(f) are replaced with portions of reference signal R(f). Reference signal adjustment module 1035 is configured to provide the adjusted reference signal R(f) to primary microphone wind noise suppression module 1015 via adjusted reference signal 1040.

In one embodiment, reference signal adjustment module 1035 separately estimates the difference in one or more of delay, gain, spectral shape, and background noise level between primary signal P(f) and reference signal R(f) and separately adjusts the one or more parameters of reference signal R(f), based on the estimates, to more closely match the corresponding parameters of primary signal P(f).

In another embodiment, reference signal adjustment module 1035 adjusts one or more of the delay, gain, and spectral shape of reference signal R(f) using a single adaptive filter in the time domain. Such an adaptive filter can filter reference signal R(f) to adjust one or more of these parameters to better match the corresponding parameters of primary signal P(f). For example, the adaptive filter can filter reference signal R(f) to adjust its delay and gain to better match the delay and gain of primary signal P(f).

In an embodiment, the filter taps of the adaptive filter are adapted only when wind noise is absent or below some threshold in primary signal P(f) and is absent or below some threshold in reference signal R(f) such that the filtered reference signal effectively tracks the speech characteristics of primary signal P(f). In this embodiment, when wind noise is present or above some threshold in primary signal P(f) and absent or below some threshold in reference signal R(f), adaptation of the filter taps is stopped, and the adaptive filter is used to filter reference signal R(f). The adaptively filtered reference signal R(f) is then used by primary microphone wind noise suppression module 1015 to replace (at least a portion of) the wind noise corrupted frame of primary signal P(f).

In yet another embodiment, if wind noise detection and suppression module 305 is implemented in a noise suppression system that implements a time-varying blocking matrix in the frequency domain, similar to blocking matrix 315 described in FIG. 3, then reference signal adjustment module 1030 can adjust one or more of the delay, gain, and spectral shape of reference signal R(f) using a filter derived from the inverse filter function of the blocking matrix. As discussed above, in regard to blocking matrix 315 illustrated in FIG. 3, the primary function of such a time-varying blocking matrix is to estimate and remove the undesirable speech component in reference signal R(f) to get a "cleaner" noise reference signal. More specifically, the time-varying blocking matrix filters primary signal P(f) to provide an estimate of the undesirable speech component in reference signal R(f) and then subtracts the estimate from reference signal R(f) to provide a cleaner noise reference signal (with the speech component suppressed).

Because the first filter module 325 in the time-varying blocking matrix filters the primary signal P(f) to approximate the speech signal in the reference signal R(f), the inverse filter function of the first filter module 325 should achieve the opposite effect. In other words, filtering the speech component in reference signal R(f), using the inverse filter function of the first filter module 325, should provide an approximation of primary signal P(f).

Furthermore, in a noise suppression system that implements a time-varying blocking matrix in the frequency domain, such as noise suppression system 300 illustrated in FIG. 3, the time-varying blocking matrix is adapted and readily available and, when it includes a single complex-tap per sub-band, the inverse filter function corresponding to the first filter module 325 can be obtained by simply taking the reciprocal of the weights assigned to the complex-taps. Thus, implementing an inverse filter function of the first filter module 325 can be a very low-complexity and elegant way to filter the reference signal R(f) to adjust its delay, gain, and/or spectral shape before using it to replace a portion of primary signal P(f) corrupted by wind noise.

One issue that has not yet been discussed in detail is how reference signal adjustment module 1035 can adjust the acoustic background noise level of reference signal R(f) to better match the acoustic background noise level of primary signal P(f). In general, in a typical dual-microphone configuration with a primary microphone (e.g., primary microphone 104) and a noise reference microphone (e.g., reference microphone 106), the signal-to-noise ratio (SNR) of the signal picked up by the noise reference microphone is usually lower than the SNR of the signal picked up by the primary microphone. In other words, the background noise level is usually higher relative to the speech signal level in the signal picked up by the noise reference microphone than it is in the signal picked up by the primary microphone. Thus, for example, after the gain of reference signal R(f) is adjusted to better match the speech signal level of primary signal P(f), the acoustic background noise level in the adjusted reference signal 1040 will typically be higher than the acoustic background noise level in primary signal P(f). The adaptive filtering approaches described above (whether implemented in the time-domain or frequency-domain) generally only adjust the delay, gain, and spectral shape of reference signal R(f) and do not adjust the acoustic background noise level to compensate for this anticipated difference.

In one embodiment, to adjust the acoustic background noise level of reference signal R(f) to better match the acoustic background noise level of primary signal P(f), reference signal adjustment module 1035 estimates the long-term average acoustic background noise levels and speech levels in both primary signal P(f) and reference signal R(f). From these estimated levels, reference signal adjustment module 1035 calculates a long-term signal-to-noise ratio (SNR) for each signal.

Reference signal adjustment module 1035 is then configured to use these calculated, long-term SNR values in combination with a single-channel noise suppression technique to suppress the acoustic background noise level in reference signal R(f) to better match the acoustic background noise level in primary signal P(f). Any suitable single-channel noise suppression technique can be used, but to make the acoustic background noise level of reference signal R(f) roughly the same as the acoustic background noise level of primary signal P(f), the target amount of noise suppression can be set to (or determined based on) the difference between the calculated, long-term SNR of primary signal P(f) and the calculated, long-term SNR of reference signal R(f).

After applying single-channel noise suppression to reference signal R(f) with the amount of noise suppression set to (or at least based on) SNR1-SNR2, where SNR1 and SNR2 are the calculated, long-term SNR values of primary signal P(f) and reference signal R(f), respectively, the resulting noise-suppressed reference signal R(f) should have roughly the same level of acoustic background noise as primary signal P(f). This is important for maintaining a consistent level of acoustic background noise in the final wind noise suppressed primary signal P(f). Without such background noise level matching, the wind noise suppressed primary signal P(f) can have an acoustic background noise level that modulates with the application of waveform substitution performed by primary microphone wind noise suppression module 1015.

To avoid potential waveform discontinuities at the boundaries between primary signal P(f) and a substituted waveform, primary microphone wind noise suppression module 1015 can perform proper overlap-add operations between primary signal P(f) and the substituted waveform. For example, when a wind noise corrupted portion of primary signal P(f) is substituted for a comparatively cleaner portion of an adaptively filtered reference signal R(f) (provided by reference signal adjustment module 1035), primary microphone wind noise suppression module 1015 can smooth the boundaries between the portion of the adaptively filtered reference signal R(f) and primary signal P(f) using proper overlap-add operations.

A general, overlap-add operation of two signals can be defined by:

$$s(n)=s_{out}(n)\cdot w_{out}(n)+s_{in}(n)\cdot w_{in}(n);n=0\ldots N-1$$

where $s_{out}$ is the signal to be faded out, $s_{in}$ is the signal to be faded in, $w_{out}$ is the fade-out window, $w_{in}$ is the fade-in window, and N is the overlap-add window length. The general overlap-add operation, defined by the above equation, can be used to smoothly merge primary signal P(f) with a substituted waveform. In addition, any suitable fade-in window, fade-out window, and overlap-add window length can be used.

Figure 11:
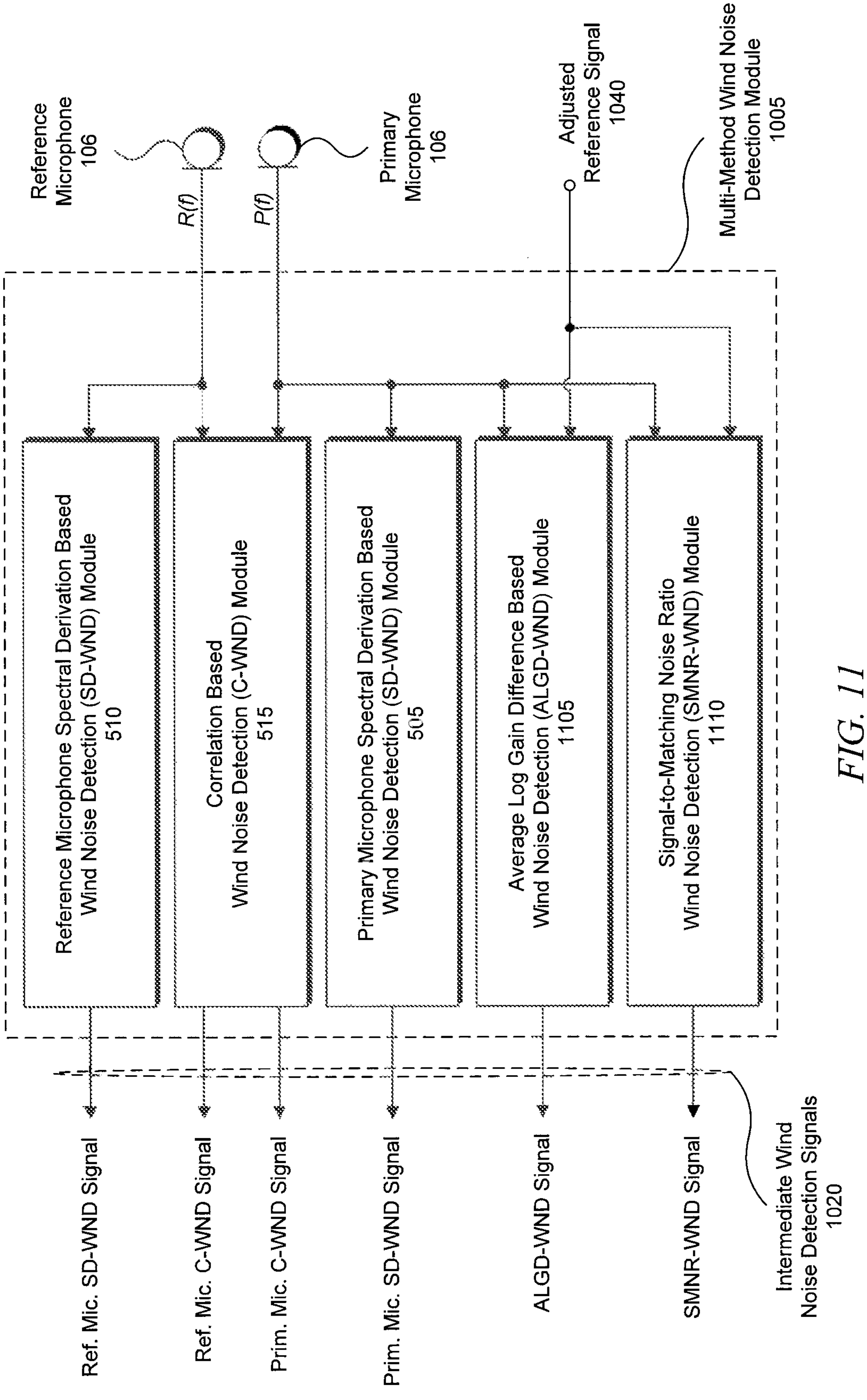
FIG. 11 illustrates a block diagram of another example multi-method wind noise detection module in accordance with embodiments of present invention.

FIG. 11 illustrates an exemplary block diagram of multi-method wind noise detection module 1005 in accordance with embodiments of present invention. As illustrated in FIG. 11, multi-method wind noise detection module 1005 includes a primary microphone spectral derivation based wind noise detection (SD-WND) module 505, a reference microphone SD-WND module 510, a correlation based wind noise detection (C-WND) module 515, an average log gain difference based wind noise detection (ALGD-WND) module 1105, and a signal-to-matching-noise ratio wind noise detection (SMNR-WND) module 1110. These modules each perform wind noise detection on a frame-by-frame basis of primary signal P(f) and/or reference signal R(f) and provide intermediate wind noise detection signals 1020 as output that indicates whether wind noise is present or absent in a frame currently being analyzed. It should be noted that one or more of the wind noise detection modules can be omitted from multi-method wind noise detection module 1005 in other embodiments.

Turning now to the description of SD-WND module 505, which was described previously in regard to FIG. 5, it can be shown that the expected spectrum of wind noise has an envelope that decays in a roughly linear fashion with frequency. SD-WND module 505 is configured to exploit this characteristic of wind noise to detect its presence or absence in primary signal P(f). More specifically, SD-WND module 505 is configured to compare the spectrum of a frame of primary signal P(f) with an expected wind noise spectrum having the characteristics noted above (i.e., a spectrum with a magnitude that decreases with frequency and an overall spectral shape that is close to linear). If a difference in the spectrums is greater than a certain threshold, SD-WND module 505 determines that wind noise is absent in primary signal P(f). Otherwise, SD-WND module 505 determines that wind noise is present in primary signal P(f).

In one embodiment, SD-WND module 505 is configured to compare the magnitude or energy of certain frequencies of a frame of primary signal P(f) to corresponding magnitudes or energies of an expected wind noise spectrum. For example, because wind noise is often concentrated in the lower frequency range of speech (e.g., <2250 Hz), SD-WND module 505 can compare the magnitude or energies of only those frequencies of primary signal P(f), within the lower frequency range of speech, to corresponding magnitudes or energies of the expected wind noise spectrum. If a difference in magnitude or energy between the spectrums is greater than a certain threshold, then SD-WND module 505 determines that wind noise is absent in primary signal P(f). Otherwise, SD-WND module 505 determines that wind noise is present in primary signal P(f). Primary microphone SD-WND module 505 provides, as output, primary microphone SD-WND signal that indicates whether wind noise is present or absent in the frame of primary signal P(f).

SD-WND module 510 is configured to operate in a similar manner as SD-WND module 505. However, SD-WND module 510 is configured to detect the presence or absence of wind noise in a frame of reference signal R(f). SD-WND module 510 provides, as output, reference microphone SD-WND signal that indicates whether wind noise is present or absent in the frame of samples of reference signal P(f).

It should be noted that spectral derivation based wind noise detection is a single channel method and is applied on primary signal P(f) and reference signal R(f) separately (i.e., without using the information contained in the other signal). In addition, it should be noted that the thresholds used by SD-WND modules 505 and 510, to determine whether wind noise is present or absent in primary signal P(f) and reference signal R(f), can be different in value.

Turning now to the description of C-WND module 515, which was also described previously in regard to FIG. 5, the following three facts are exploited by C-WND module 515 to detect whether wind noise is present or absent in primary signal P(f) and reference signal R(f): (1) wind noise typically does not correlate well with acoustic sounds (e.g., speech or background noise); (2) acoustic sounds picked up by a first microphone (e.g., primary microphone 104 illustrated in FIG. 1) typically will correlate well with acoustic sounds picked up by a second microphone that is located in the same general area as the first microphone (e.g., reference microphone 106 illustrated in FIG. 2); and (3) for voiced speech, speech in one portion of a signal picked up by a microphone typically will correlate well with speech in another portion of the same signal one pitch period earlier. In general, voiced speech is nearly periodic and the period of voiced speech at any given moment is referred to as the pitch period. Thus, a frame of samples of a signal containing voiced speech typically correlates well with a similarly sized frame of samples of the same signal from one pitch period earlier. Voiced speech can be generated, for example, by the vocal tract of a speaker when the speaker sounds out a vowel.

Using the three facts noted above, C-WND module 515 detects whether wind noise is present or absent in primary signal P(f) and reference signal R(f), on a frame-by-frame basis, by examining the relationship between: (i) the maximum normalized correlation of primary signal P(f) in an estimated pitch period range; (ii) the maximum normalized correlation of reference signal R(f) in an estimated pitch period range; and (iii) the cross-channel normalized correlation between primary signal P(f) and reference signal R(f).

In one embodiment, if all three of these correlation values are above some defined threshold, it is assumed that primary signal P(f) and reference signal R(f) include voiced speech and wind noise is not present in either primary signal P(f) or reference signal R(f).

In another embodiment, if the cross-channel correlation value in (iii) is above the defined threshold and the same-channel correlation values in (i) and (ii) are below the defined threshold, it is assumed that primary signal P(f) and reference signal R(f) include unvoiced speech and/or background noise and wind noise is not present in either primary signal P(f) or reference signal R(f).

In yet another embodiment, if one of the two same-channel correlation values determined in (i) and (ii) is above the defined threshold and the other is below the defined threshold, and the cross-channel correlation value in (iii) is also below the defined threshold, then it is assumed that wind noise is present in the signal with the same-channel correlation value below the defined threshold and that wind noise is not present in the signal with the same-channel correlation value above the defined threshold (or at least to a much less extent).

It should be noted that different defined thresholds can be used for comparison against each correlation value. It should be further noted that the relative differences, between the three correlation values, can be further used to detect whether wind noise is present or absent in primary signal P(f) and reference signal R(f). For example, in addition to requiring all three correlation values be above some defined threshold in order to assume that wind noise is not present in either primary signal P(f) or reference signal R(f), it can be further required that the relative difference in value between one or more of the correlation values be within some defined range. In addition, it should be further noted that the three correlation values can be non-normalized in other embodiments.

C-WND module 515 provides, as output, two intermediate wind noise detection signals 1020 based on the relationship between the correlation values as outlined above. More specifically, C-WND module 515 provides a primary microphone C-WND signal and a reference microphone C-WND signal, as output, to respectively indicate whether wind noise is present or absent in primary signal P(f) and reference signal R(f).

Turning now to the description of ALGD-WND module 1105, ALGD-WND module 1105 is configured to detect the presence or absence of wind noise in primary signal P(f) and adjusted reference signal 1040 based on the average value of the logarithmic gain difference between corresponding frequency components of primary signal P(f) and adjusted reference signal 1040. Adjusted reference signal 1040 has been generated by reference signal adjustment module 1030, illustrated in FIG. 10, by adjusting one or more of the delay, gain, spectral shape, and acoustic background noise of reference signal R(f) to better match those parameters of primary signal P(f).

In general, wind noise picked up by primary microphone 104 (which provides primary signal P(f)) or reference microphone 106 (which provides reference signal R(f)) often will not be picked up (or at least not to the same extent) by the other microphone because air turbulence caused by wind is usually a fairly local event. Therefore, a difference in energy between corresponding sub-bands of primary signal P(f) and adjusted reference signal 1040 (which was generated based on reference signal R(f)) can provide a good indication as to whether wind noise is present or absent in each signal.

In one embodiment, ALGD-WND module 1105 is configured to receive each frame of primary signal P(f) and adjusted reference signal 1040 already transformed into the frequency domain. In another embodiment, ALGD-WND module 1105 is configured to receive each frame of primary signal P(f) and adjusted reference signal 1040 in the time domain and is configured to calculate the discrete Fourier transform (DFT) of each frame to transform the frames into the frequency domain. ALGD-WND module 1105 can calculate the DFT using, for example, the Fast Fourier Transform (FFT). In general, the resulting frequency domain signal describes the magnitudes and phases of component cosine waves (also referred to as component frequencies) that make up the time domain frame, where each component cosine wave corresponds to a particular frequency between DC and one-half the sampling rate used to obtain the time domain frame.

For example, and in one embodiment, each time domain frame of primary signal P(f) and adjusted reference signal 1040 includes 128 samples and is transformed into the frequency domain using a 128-point DFT by ALGD-WND module 1105 or some other module not shown. The 128-point DFT provides 65 values that represent the magnitudes of the component cosine waves that make up the time domain frame. In another embodiment, each time domain frame of primary signal P(f) and adjusted reference signal 1040 includes N samples and is transformed into the frequency domain using an M-point DFT by ALGD-WND module 1105 or some other module not shown, where N and M are integer numbers and M is greater than or equal to N. When M is larger than N, the N samples of primary signal P(f) and adjusted reference signal 1040 can be padded with M-N zeroes.

Once the magnitudes of the component cosine waves are obtained for a frame of primary signal P(f) and for a frame of adjusted reference signal 1040, ALGD-WND module 1105 is configured to group the component cosine waves into sub-bands, where a sub-band can include one or more component cosine waves. Component cosine waves assigned to a particular sub-band can be grouped by adding their corresponding energies together or the logarithm of their corresponding magnitudes together. The resulting sum represents an estimated energy of the sub-band. For sub-bands that contain single component cosine waves (which can be all of them in one embodiment), the estimated energy of these sub-bands can simply be set equal to the magnitude of their respective component cosine waves or the logarithm of the magnitude of their respective component cosine waves.

In one embodiment, ALGD-WND module 1105 is configured to determine a difference in energy between corresponding sub-bands of primary signal P(f) and adjusted reference signal 1040 by dividing the calculated sub-band energies of primary signal P(f) by corresponding sub-band energies of adjusted reference signal 1040. In another embodiment, ALGD-WND module 1105 is configured to determine a difference in energy between corresponding sub-bands of primary signal P(f) and adjusted reference signal 1040 by subtracting the sub-band energies of adjusted reference signal 1040 from corresponding sub-band energies of primary signal P(f) to determine differences in energy.

In another embodiment, ALGD-WND module 1105 is configured to determine a difference in energy between corresponding sub-bands of primary signal P(f) and adjusted reference signal 1040 for sub-bands corresponding only to a lower frequency range of speech. As discussed above, the expected spectrum of wind noise has an envelope that decays in a roughly linear fashion with frequency and is often concentrated in the lower frequency range of speech (e.g., <2250 Hz). Therefore, upper sub-bands that correspond to higher frequencies of speech (e.g., >2250 Hz) can be ignored because wind noise generally does not corrupt those frequencies.

Once the differences in energy between corresponding sub-bands of primary signal P(f) and adjusted reference signal 1040 are determined, ALGD-WND module 1105 can average the differences in energy together and provide the result as output via ALGD-WND signal. Assuming that adjusted reference signal 1040 matches primary signal P(f) signal well in terms of delay, gain, spectral shape, and background noise level, an ALGD-WND signal around 0 dB indicates that adjusted reference signal 1040 and primary signal P(f) are matching well and there is little or no wind noise in either signal. A large positive ALGD-WND signal indicates that there is wind noise in primary signal P(f) signal and no wind noise in adjusted reference signal 1040, or that primary signal P(f) has more wind noise than adjusted reference signal 1040. Conversely, a large negative ALGD-WND signal indicates that there is wind noise in adjusted reference signal 1040 and not in primary signal P(f), or adjusted reference signal 1040 has more wind noise than primary signal P(f).

Turning now to the description of SMNR-WND module 1110, SMNR-WND module 1110 is configured to divide the energy of primary signal P(f) by the energy of the difference between primary signal P(f) and adjusted reference signal 1040 to obtain a special SNR value referred to as the signal-to-matching-noise ratio (SMNR). Assuming that adjusted reference signal 1040 matches primary signal P(f) well in terms of delay, gain, spectral shape, and background noise level, then the calculated SMNR value should be large when there is little or no wind noise present in either primary signal P(f) and adjusted reference signal 1040. For example, the calculated SMNR value can be on the order of 30 to 50 dB when there is little or no wind noise present in either primary signal P(f) or adjusted reference signal 1040. On the other hand, when there is wind noise present in primary signal P(f) or adjusted reference signal 1040, the calculated SMNR value should be comparatively smaller. Thus, a small SMNR indicates there is likely wind noise in one of the two signals, while a large SMNR indicates there is likely little or no wind noise present in either of the two signals.

Figure 12:
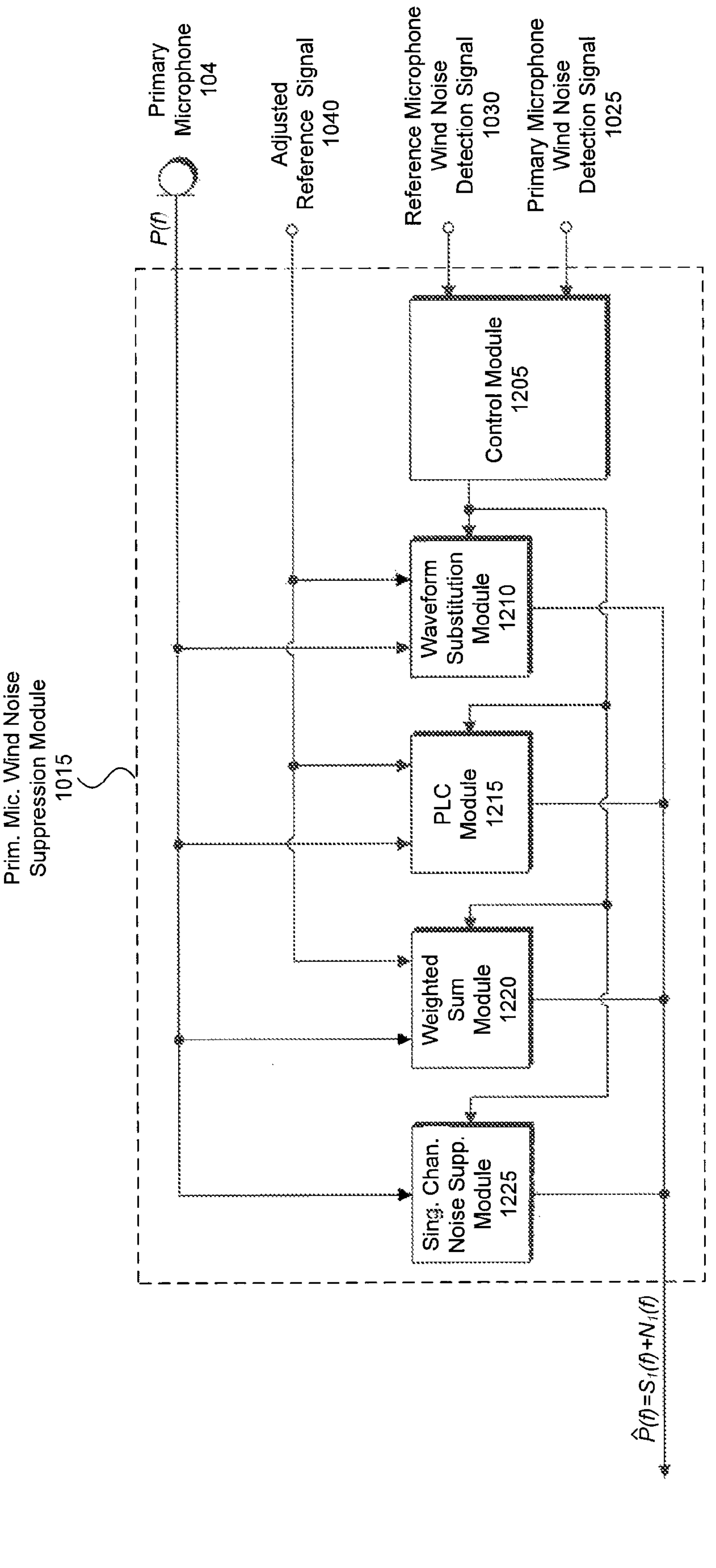
FIG. 12 illustrates a block diagram of another primary microphone wind noise suppression module in accordance with embodiments of present invention.

Referring now to FIG. 12, an example implementation of primary microphone wind noise suppression module 1015 is illustrated in accordance with embodiments of the present invention. Primary microphone wind noise suppression module 1015 is configured to perform wind noise suppression on primary signal P(f) on a frame-by-frame basis to provide, as output, wind noise suppressed primary signal PT. As illustrated in FIG. 12, wind noise suppression module 1015 includes a control module 1205 and a waveform substitution module 1210. Waveform substitution module 1210 is configured to replace (at least a portion of) a wind noise corrupted frame of primary signal P(f) with (at least a portion of) a comparatively cleaner frame of adjusted reference signal 1040 as described above in FIG. 10. In addition, wind noise suppression module 1015 optionally further includes one or more of packet loss concealment (PLC) module 1215, weighted sum module 1220, and single-channel noise suppression module 1225.

In operation, control module 1205 is configured to receive primary microphone wind noise detection signal 1025 and reference microphone wind noise detection signal 1030 that respectively indicate whether wind noise is present or absent in primary signal P(f) and reference signal R(f) (and, thereby, whether wind noise is present or absent in adjusted reference signal 1040). Based on these two signals, control module 1205 controls the operation of waveform substitution module 1210 and, if included, PLC module 1215, weighted sum module 1220, and single channel noise suppression module 1225. More specifically, based on different wind noise scenarios indicated by primary microphone wind noise detection signal 1025 and reference microphone wind noise detection signal 1030, control module 1205 use a different one of waveform substitution module 1210, PLC module 1215 weighted sum module 1220, and single channel noise suppression module 1225 to suppress wind noise in primary signal P(f) or make primary signal P(f) more consistent across time. The resulting signals from these modules are provided as output via wind noise suppressed primary signal $\hat{P}(f)$.

Different responses of control module 1205 to each wind noise scenario are described further below under the assumption that primary microphone wind noise suppression module 1015 is implemented in noise suppression system 300 illustrated in FIG. 3 (or some other similar noise suppression system), which includes an acoustic noise suppression module 310 for suppressing acoustic background noise in primary signal P(f) after wind noise detection has been performed. It should be noted that this assumption is provided by way of example and not limitation.

In a first scenario, when primary microphone wind noise detection signal 1025 and reference microphone wind noise detection signal 1030 indicate that wind noise is absent or below some threshold in primary signal P(f) and reference signal R(f) (and, thereby, absent or below some threshold in adjusted reference signal 1040), control module 1205 is configured to bypass waveform substitution module 1210 and, if included, PLC module 1215, weighted sum module 1220, and single channel noise suppression module 1225. In this scenario, control module 1205 is configured to set wind noise suppressed primary signal $\hat{P}(f)$ equal to primary signal P(f). Although not shown in FIG. 12, control module 1205 can set wind noise suppressed primary signal $\hat{P}(f)$ equal to primary signal P(f) using a bypass module that simply passes primary signal P(f) straight through to suppressed primary signal $\hat{P}(f)$.

Acoustic noise suppression module 310, illustrated in FIG. 3, would then perform acoustic noise suppression in the usual way: blocking matrix 315 would suppress the speech component in reference signal R(f), and the speech-suppressed version of reference signal R(f) would then be passed through ANC 320 to approximate the noise component in primary signal P(f) and subtract the approximate noise component from primary signal P(f) to cancel out (at least a portion of) any acoustic background noise.

In a second scenario, when primary microphone wind noise detection signal 1025 indicates that wind noise is absent or below some threshold in primary signal P(f) and reference microphone wind noise detection signal 1030 indicates that wind noise is present or above some threshold in reference signal R(f) (and, thereby, present or above some threshold in adjusted reference signal 1040), control module 1205 is configured to bypass waveform substitution module 1210 and, if included, PLC module 1215 and weighted sum module 1220.

In this second scenario, acoustic noise suppression module 310, illustrated in FIG. 3, can be restricted from performing acoustic noise suppression on primary signal P(f). This is because reference signal R(f) has wind noise and ANC 320 cannot effectively reduce the acoustic background noise in primary signal P(f) using reference signal R(f) when reference signal R(f) is corrupted by wind noise. In fact, performing acoustic noise suppression using a wind noise corrupted reference signal R(f) can actually worsen the quality of primary signal P(f).

However, simply restricting acoustic noise suppression module 310 from performing acoustic noise suppression can lead to its own problems. For example, if acoustic noise suppression module 310 provides, on average, X dB of acoustic noise reduction when wind noise is absent or below some threshold in both primary signal P(f) and reference signal R(f), simply turning ANC 320 off when wind noise is present or above some threshold in reference signal R(f) will cause the acoustic background noise level in primary signal P(f) to be X dB higher in the regions where reference signal R(f) is corrupted by wind noise. If this is not dealt with, the acoustic background noise level in primary signal P(f) will modulate with the presence of wind noise in reference signal R(f).

To combat this problem, control module 1205 can use single-channel noise suppression module 1225 to apply single-channel noise suppression with X dB of target noise suppression to primary signal P(f) during this second wind noise scenario. Doing so will help to maintain a roughly constant background noise level. Single-channel noise suppression module 1225 provides this single-channel noise suppressed signal, as output, via wind noise suppressed primary signal $\hat{P}(f)$.

In the third scenario, when primary microphone wind noise detection signal 1025 indicates that wind noise is present or above some threshold in primary signal P(f) and reference microphone wind noise detection signal 1030 indicates that wind noise is absent or below some threshold in reference signal R(f) (and, thereby, absent or below some threshold in adjusted reference signal 1040), control module 1205 is configured to use waveform substitution module 1210 to replace (at least a portion of) the wind noise corrupted frame of primary signal P(f) with (at least a portion of) the comparatively cleaner frame of adjusted reference signal 1040 as described above in FIG. 10. Waveform substitution module 1210 provides the waveform substituted primary signal P(f), as output, via wind noise suppressed primary signal $\hat{P}(f)$.

In the fourth and final scenario, when both primary microphone wind noise detection signal 1025 and reference microphone wind noise detection signal 1030 indicate that wind noise is present or above some threshold in primary signal P(f) and reference signal R(f) (and, thereby, present or above some threshold in adjusted reference signal 1040), control module 1205 can apply Packet Loss Concealment (PLC) using PLC module 1215 and/or can perform a weighted sum method using weighted sum module 1220 to suppress wind noise in primary signal P(f).

For example, if the wind noise does not last too long in both primary signal P(f) and reference signal R(f), control module 1205 can use PLC module 1215 to perform PLC techniques to replace a current frame of primary signal P(f) with an extrapolated version of the current frame from previous frame(s) of primary signal P(f) that were not corrupted by wind noise. Such a PLC-based method, however, often works well only when the time period of wind noise does not last too long. For example, if the burst of wind noise lasts less than about 20 ms, the PLC-based method can be quite effective. If the burst of wind noise lasts about 20 to 40 ms, the output audio quality from the PLC-based method varies depending on whether the speech signal segment of primary signal P(f), corrupted by wind noise, is sufficiently stationary. If the burst of wind noise lasts more than about 40 to 60 ms, the PLC-based method tends to produce unnatural tonal distortion. Hence, if wind noise lasts 40 ms the output signal of PLC module 1215 should be ramped down toward zero or some other method should be used.

It should be noted that if the wind noise is only moderate so that it is still possible to estimate the pitch period and the signal gain from the wind-noise-corrupted portion of primary signal P(f), then PLC module 1215 can perform a modified version of the PLC-based method. In a traditional PLC method, the waveform of a frame is completely lost and the waveform extrapolation can only be based on the waveform in the previous frame(s). In the present invention, if it is determined that the wind noise is only moderate in primary signal P(f) and it is still possible to estimate some speech parameters (such as the pitch period and the signal gain) of the wind-noise-corrupted portion of primary signal P(f) with reasonable reliability, then PLC module 1215 can extrapolate the waveform of previous frame(s) using speech parameters estimated from the current frame of wind-noise-corrupted primary signal P(f). As long as these speech parameters can be estimated with reasonable reliability, this method should work better than the traditional PLC-based method, not only in that the audio quality will be better, but also in that the extrapolation of the waveform can likely be performed for a wind burst with longer duration.

Moreover, if one of the microphone signals (i.e., primary signal P(f) and reference signal R(f)) has a lesser degree of wind noise and can be used to estimate such speech parameters more reliably than using the other microphone signal, then the PLC operation can be performed by PLC module 1215 based on estimated speech parameters of the microphone signal with a lesser degree of wind noise.

If the wind noise in both microphone signals last longer than the PLC-based method can handle, control module 1205 can use weighted sum module 1220 to suppress wind noise in primary signal P(f) during the fourth wind noise scenario. Weighted sum module 1220 is specifically configured to weight primary signal P(f) and adjusted reference signal 1040 and then sum the weighted signals to suppress wind noise in primary signal P(f). The weights are assigned by weighted sum module 1220 such that the higher the relative energy of the microphone signal, the lower the weight. For example, in an ideal situation, let r be the estimated ratio of the wind noise intensity in primary signal P(f) over the wind noise intensity in adjusted reference signal 1040, then the weight for primary signal P(f) can be chosen as:

$$w_1 = \frac{1/r}{r + 1/r} = \frac{1}{r^2 + 1}$$

and the weight for the secondary microphone signal can be chosen as:

$$w_2 = \frac{r}{r + 1/r} = \frac{r^2}{r^2 + 1}.$$

Such a weighted sum will tend to have an output signal biased toward the microphone signal that has a lesser degree of wind noise relative to the speech level. Thus, when the relative intensity of wind noise changes dynamically between the two signals (i.e., primary microphone signal P(f) and adjusted reference signal 1040), this weighted sum output signal will always and automatically "steer" toward the signal with a lesser degree of wind noise.

If the wind noise in the two signals is equally strong relative to the speech level in each, we have $w_1=w_2=0.5$. Even in this case, the weighted sum method still gets 3 dB of improvement in the signal-to-wind-noise ratio. This is because the wind noise in the two signals are generally uncorrelated, while the speech signals from the two signals are generally in phase and are in fact almost identical. Thus, after scaling the signals by 0.5 and adding them together, the speech component in the summed up signal stays essentially unchanged in the output signal. On the other hand, after scaling the signals by 0.5 and adding them together, the wind noise component is decreased by about 3 dB compared to the unchanged level of the speech component because the wind noise in the two signals are generally uncorrelated. Hence, there is a 3 dB improvement in the signal-to-wind-noise ratio after the weighted sum method is performed by weighted sum module 1220.

If the wind noise intensity ratio r is difficult to estimate reliably, weighted sum module 1220 can alternatively use the ratio of the energy values of primary signal P(f) and adjusted reference signal 1040 averaged over some frequency subbands as a rough substitute. However, in this case care should be taken to detect the condition when the noise reference microphone is covered, for example, by a user's hand or finger, which greatly reduces the level of adjusted reference signal 1040. If this situation is detected, the weighted sum method above can be bypassed to prevent the primary microphone signal from being wiped out.

Figure 13:
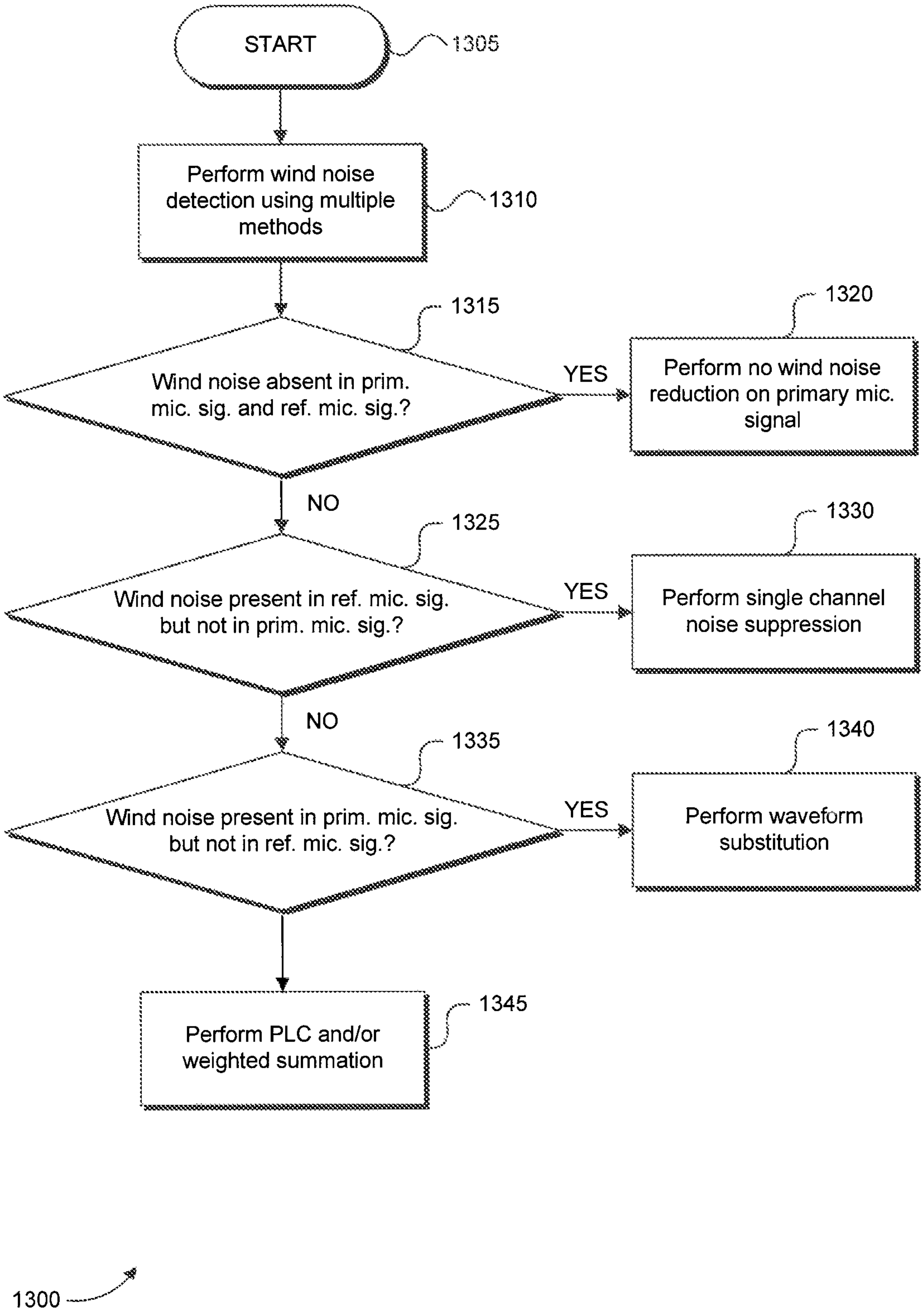
FIG. 13 illustrates a flowchart of another example multi-microphone method for wind noise detection and suppression in accordance with embodiments of present invention.

Referring now to FIG. 13, a flowchart 1300 of an example method for multi-microphone wind noise detection and suppression in accordance with embodiments of present invention is illustrated. The method of flowchart 1300 can be implemented by wind noise detection and suppression module 305 as described above and illustrated in FIG. 10. However, it should be noted that the method can be implemented by other systems and components as well. It should be further noted that some of the steps of flowchart 1300 do not have to occur in the order shown in FIG. 13.

The method of flowchart 1300 begins at step 1305 and transitions to step 1310. At step 1310, wind noise detection is performed on primary signal P(f) and reference signal R(f) using multiple methods. More specifically, at step 1310 wind noise detection is performed to detect the presence or absence of wind noise in primary signal P(f) using two or more wind noise detection methods and to detect the presence or absence of wind noise in reference signal R(f) using two or more wind noise detection methods. Each wind noise detection method produces a wind noise detection signal that indicates whether wind noise is present or absent. For example, one or more of the following methods can be performed to determine if primary signal P(f) or reference signal R(f) contain wind noise: spectral-deviation based wind noise detection, correlation based wind noise detection, average log gain difference based wind noise detection, and signal-to-matching wind noise detection. The resulting wind noise detection signals corresponding to primary signal P(f) are then combined to produce a single wind noise detection signal for primary signal P(f), and the resulting wind noise detection signals corresponding to reference signal P(f) are then combined to produce a single wind noise detection signal for reference signal R(f). Further details regarding wind noise detection using multiple methods were described above in regard to FIGS. 10 and 11 and are incorporated here by reference.

At step 1315, a determination is made as to whether wind noise is absent or below a threshold in both primary signal P(f) and reference signal R(f), as indicated by the wind noise detection signals produced at step 1310. If wind noise is absent or below a threshold in both primary signal P(f) and reference signal R(f), flowchart 1300 proceeds to step 1320 where no wind noise reduction is performed on primary signal P(f). Otherwise, flowchart 1300 proceeds to step 1325.

At step 1325, a determination is made as to whether wind noise is present or above a threshold in reference signal R(f) and absent or below a threshold in primary signal P(f), as indicated by the wind noise detection signals produced at step 1310. If wind noise is present or above a threshold in reference signal R(f) and absent or below a threshold in primary signal P(f), flowchart 1300 proceeds to step 1330 where single channel noise suppression is performed using single channel noise suppression module 1225 as discussed above in regard to FIG. 12. Otherwise, flowchart 1300 proceeds to step 1335.

At step 1335, a determination is made as to whether wind noise is present or above a threshold in primary signal P(f) and absent or below a threshold in reference signal R(f), as indicated by the wind noise detection signals produced at step 1310. If wind noise is present or above a threshold in primary signal P(f) and absent or below a threshold in reference signal R(f), flowchart 1300 proceeds to step 1340 where waveform substitution is performed using waveform substitution module 1210 as discussed above in regard to FIG. 12. Otherwise, flowchart 1300 proceeds to step 1345.

At step 1345, it is assumed that wind noise is present or above a threshold in both primary signal P(f) and reference signal R(f). In this instance, when wind noise is present or above a threshold in both primary signal P(f) and reference signal R(f), PLC is performed using PLC module 1215 as discussed above in regard to FIG. 12 and/or weighted summation is performed using weighted sum module 1220 as further discussed above in regard to FIG. 12.

V. Example Computer System Implementation

It will be apparent to persons skilled in the relevant art(s) that various elements and features of the present invention, as described herein, can be implemented in hardware using analog and/or digital circuits, in software, through the execution of instructions by one or more general purpose or special-purpose processors, or as a combination of hardware and software.

Figure 14:
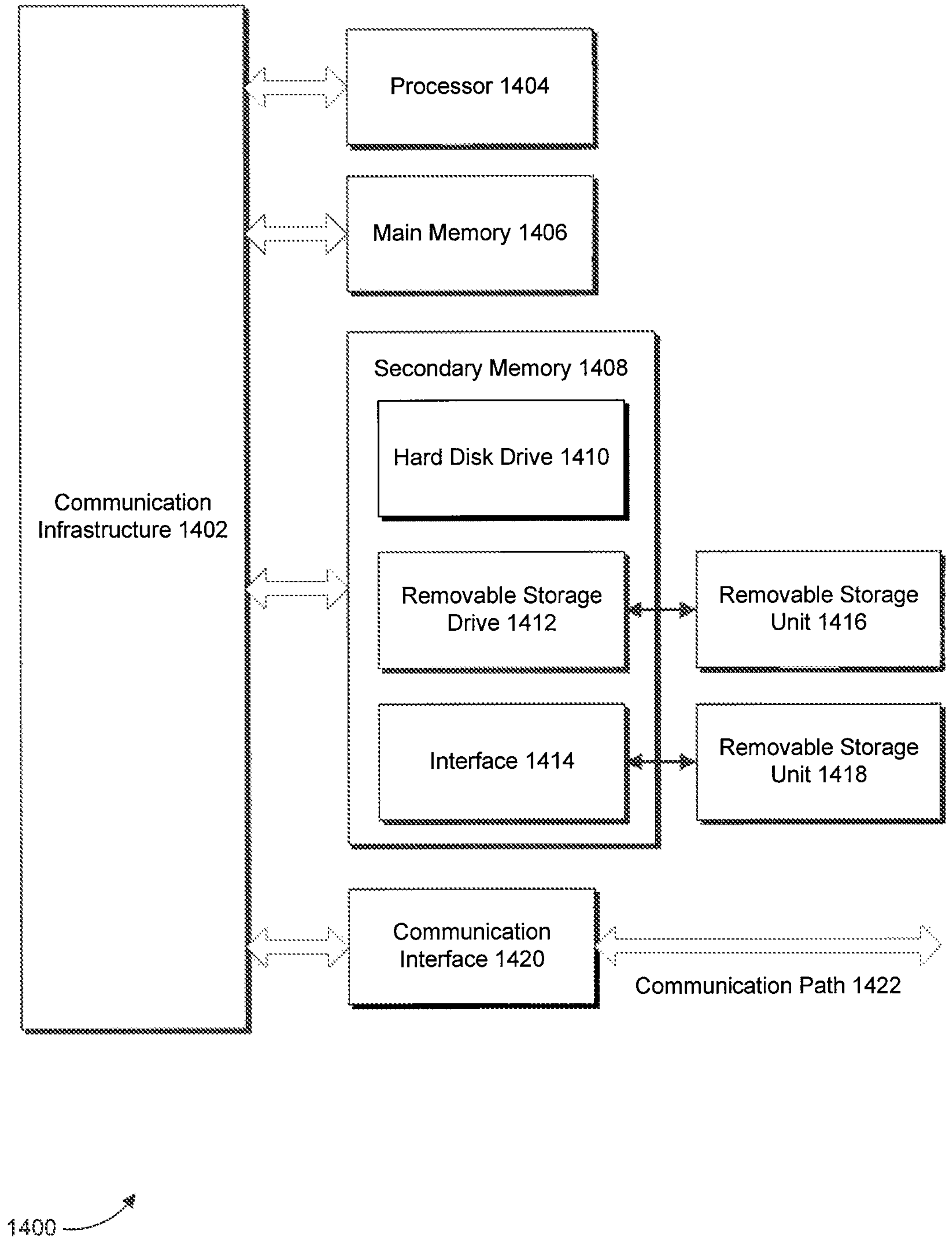
FIG. 14 illustrates a block diagram of an example computer system that can be used to implement aspects of the present invention.

The following description of a general purpose computer system is provided for the sake of completeness. Embodiments of the present invention can be implemented in hardware, or as a combination of software and hardware. Consequently, embodiments of the invention may be implemented in the environment of a computer system or other processing system. An example of such a computer system 1400 is shown in FIG. 14. All of the modules depicted in FIGS. 3-5, 7, and 10-12, for example, can execute on one or more distinct computer systems 1400. Furthermore, each of the steps of the flowcharts depicted in FIGS. 6, 9 and 13 can be implemented on one or more distinct computer systems 1400.

Computer system 1400 includes one or more processors, such as processor 1404. Processor 1404 can be a special purpose or a general purpose digital signal processor. Processor 1404 is connected to a communication infrastructure 1402 (for example, a bus or network). Various software implementations are described in terms of this exemplary computer system. After reading this description, it will become apparent to a person skilled in the relevant art(s) how to implement the invention using other computer systems and/or computer architectures.

Computer system 1400 also includes a main memory 1406, preferably random access memory (RAM), and may also include a secondary memory 1408. Secondary memory 1408 may include, for example, a hard disk drive 1410 and/or a removable storage drive 1412, representing a floppy disk drive, a magnetic tape drive, an optical disk drive, or the like. Removable storage drive 1412 reads from and/or writes to a removable storage unit 1416 in a well-known manner Removable storage unit 1416 represents a floppy disk, magnetic tape, optical disk, or the like, which is read by and written to by removable storage drive 1412. As will be appreciated by persons skilled in the relevant art(s), removable storage unit 1416 includes a computer usable storage medium having stored therein computer software and/or data.

In alternative implementations, secondary memory 1408 may include other similar means for allowing computer programs or other instructions to be loaded into computer system 1400. Such means may include, for example, a removable storage unit 1418 and an interface 1414. Examples of such means may include a program cartridge and cartridge interface (such as that found in video game devices), a removable memory chip (such as an EPROM, or PROM) and associated socket, a thumb drive and USB port, and other removable storage units 1418 and interfaces 1414 which allow software and data to be transferred from removable storage unit 1418 to computer system 1400.

Computer system 1400 may also include a communications interface 1420. Communications interface 1420 allows software and data to be transferred between computer system 1400 and external devices. Examples of communications interface 1420 may include a modem, a network interface (such as an Ethernet card), a communications port, a PCMCIA slot and card, etc. Software and data transferred via communications interface 1420 are in the form of signals which may be electronic, electromagnetic, optical, or other signals capable of being received by communications interface 1420. These signals are provided to communications interface 1420 via a communications path 1422. Communications path 1422 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 1416 and 1418 or a hard disk installed in hard disk drive 1410. These computer program products are means for providing software to computer system 1400.

Computer programs (also called computer control logic) are stored in main memory 1406 and/or secondary memory 1408. Computer programs may also be received via communications interface 1420. Such computer programs, when executed, enable the computer system 1400 to implement the present invention as discussed herein. In particular, the computer programs, when executed, enable processor 1404 to implement the processes of the present invention, such as any of the methods described herein. Accordingly, such computer programs represent controllers of the computer system 1400. Where the invention is implemented using software, the software may be stored in a computer program product and loaded into computer system 1400 using removable storage drive 1412, interface 1414, or communications interface 1420.

In another embodiment, features of the invention are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

VI. Conclusion

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

In addition, while various embodiments have been described above, it should be understood that they have been presented by way of example only, and not limitation. It will be understood by those skilled in the relevant art(s) that various changes in form and details can be made to the embodiments described herein without departing from the spirit and scope of the invention as defined in the appended claims. Accordingly, the breadth and scope of the present invention should not be limited by any of the above-described exemplary embodiments, but should be defined only in accordance with the following claims and their equivalents.

What is claimed is:

1. An apparatus for detecting and suppressing wind noise in a primary signal received by a primary microphone, the apparatus comprising:

a multi-method wind noise detection module configured to generate first and second wind noise detection signals that indicate whether wind noise is present or absent in the primary signal;

a wind noise detection signal combining module configured to combine the first and second wind noise detection signals to provide a primary microphone wind noise detection signal that indicates whether wind noise is present or absent in the primary signal; and a primary microphone wind noise suppression module configured to determine a suppression gain for a sub-band of the primary signal based on:

the primary microphone wind noise detection signal, and a comparison, performed by a suppression gain calculation module, of a difference in energy between the sub-band of the primary signal and a corresponding sub-band of a reference signal received by a reference microphone to a speech threshold and a wind threshold, wherein the speech threshold or the wind threshold is calculated based on the difference in energy and a previously calculated threshold value.

2. The apparatus of claim 1, wherein the primary microphone wind noise suppression module comprises:

an energy ratio calculation module configured to divide an estimate of the energy of the sub-band of the primary signal by an estimate of the energy of the corresponding sub-band of the reference signal to determine the difference in energy.

3. The apparatus of claim 1, wherein the primary microphone wind noise suppression module is further configured to determine the suppression gain such that the suppression gain is a constant value if the difference in energy is below the speech threshold or above the wind threshold.

4. The apparatus of claim 1, wherein the primary microphone wind noise suppression module is further configured to determine the suppression gain such that the suppression gain increases as the difference in energy increases from the speech threshold to the wind threshold.

5. The apparatus of claim 1, wherein the primary microphone wind noise suppression module is further configured to smooth the suppression gain over time.

6. The apparatus of claim 1, wherein the primary microphone wind noise suppression module further comprises:

a suppression gain mapping module configured to determine suppression gains for a group of frequency components in the sub-band of the primary signal by interpolating between the suppression gain and a suppression gain for an additional sub-band of the primary signal.

7. The apparatus of claim 1, wherein the first wind noise detection signal is generated based on the primary signal and the reference signal.

8. The apparatus of claim 1, wherein the multi-method wind noise detection module comprises:

a correlation based wind noise detection module configured to generate the first wind noise detection signal; and a spectral deviation based wind noise detection module configured to generate the second wind noise detection signal.

9. The apparatus of claim 8, wherein the correlation based wind noise detection module is configured to generate the first wind noise detection signal based on:

the correlation of a first set of samples of the primary signal with a first set of samples of the reference signal, the correlation of the first set of samples of the primary signal with a second set of samples of the primary signal, wherein the second set of samples of the primary signal are in a pitch period range of the first set of samples of the primary signal, and the correlation of the first set of samples of the reference signal with a second set of samples of the reference signal, wherein the second set of samples of the reference signal are in a pitch period range of the first set of samples of the reference signal.

10. The apparatus of claim 9, wherein the spectral deviation based wind noise detection module is configured to generate the second wind noise detection signal by comparing a frequency spectrum of the primary microphone with a frequency spectrum associated with wind noise.

11. The apparatus of claim 1, further comprising a reference microphone wind noise suppression module.

12. A method for detecting and suppressing wind noise in a primary signal received by a primary microphone, the apparatus comprising:

generating first and second wind noise detection signals that indicate whether wind noise is present or absent in the primary signal;

combining the first and second wind noise detection signals to provide a primary microphone wind noise detection signal that indicates whether wind noise is present or absent in the primary signal; and determining a suppression gain for a sub-band of the primary signal based on:

the primary microphone wind noise detection signal, and a comparison, performed by a suppression gain calculation module, of a difference in energy between the sub-band of the primary signal and a corresponding sub-band of a reference signal received by a reference microphone to a speech threshold and a wind threshold, wherein the speech threshold or the wind threshold is calculated based on the difference in energy and a previously calculated threshold value.

13. The method of claim 12, where the determining the suppression gain further comprises:

dividing an estimate of the energy of the sub-band of the primary signal by an estimate of the energy of the corresponding sub-band of the reference signal to determine the difference in energy.

14. The method of claim 12, wherein the determining the suppression gain further comprises:

determining the suppression gain such that the suppression gain is a constant value if the difference in energy is below the speech threshold or above the wind threshold.

15. The method of claim 12, wherein the determining the suppression gain further comprises:

determining the suppression gain such that the suppression gain decreases as the difference in energy increases from the speech threshold to the wind threshold.

16. The method of claim 12, further comprising:

smoothing the suppression gain over time.

17. The method of claim 12, further comprising:

determining suppression gains for a group of frequency components in the sub band of the primary signal by interpolating between the suppression gain and a suppression gain for an additional sub-band of the primary signal.

18. The method of claim 12, wherein the generating the first wind noise detection signal comprises:

generating the first wind noise detection signal based on the primary signal and the reference signal.

19. The method of claim 12, wherein the generating the first wind noise detection signal comprises:

correlating a first set of samples of the primary signal with a first set of samples of the reference signal;

correlating the first set of samples of the primary signal with a second set of samples of the primary signal, wherein the second set of samples of the primary signal are in a pitch period range of the first set of samples of the primary signal; and correlating, the first set of samples of the reference signal with a second set of samples of the reference signal, wherein the second set of samples of the reference signal are in a pitch period range of the first set of samples of the reference signal.

20. The method of claim 12, wherein generating the second wind noise detection signal comprises:

comparing a frequency spectrum of the primary microphone with a frequency spectrum associated with wind noise.

* * * * *

UNITED STATES PATENT AND TRADEMARK OFFICE

CERTIFICATE OF CORRECTION

PATENT NO. : 9,330,675 B2
APPLICATION NO. : 13/250355
DATED : May 3, 2016
INVENTOR(S) : Zhang et al.

It is certified that error appears in the above-identified patent and that said Letters Patent is hereby corrected as shown below:

Title Page, item (57), In Abstract, line 8, “that utilize this tact” with --that utilize this fact--.

In the Claims

In column 34, line 3, please replace “sub band” with --sub-band--.

In column 34, line 20, please replace “correlating, the first” with --correlating the first--.

Signed and Sealed this
Ninth Day of August, 2016

Michelle K. Lee
*Director of the United States Patent and Trademark Office*